United States Patent [19]

Kast et al.

[11] Patent Number: 5,407,896
[45] Date of Patent: Apr. 18, 1995

[54] UNSATURATED CYCLOHEXENONE OXIME ETHERS AND HERBICIDAL COMPOSITIONS THEREOF

[75] Inventors: Juergen Kast, Boehl-Iggelheim; Norbert Meyer, Ladenburg; Ulf Misslitz, Neustadt; Albrecht Harreus; Harald Rang, both of Ludwigshafen; Matthias Gerber, Mutterstadt; Helmut Walter, Obrigheim; Karl-Otto Westphalen, Speyer, all of Germany

[73] Assignee: BASF Aktiengesellschaft, Ludwigshafen, Germany

[21] Appl. No.: 10,318

[22] Filed: Jan. 28, 1993

Related U.S. Application Data

[62] Division of Ser. No. 776,044, Oct. 16, 1991, abandoned.

[30] Foreign Application Priority Data

Oct. 19, 1990 [DE] Germany .......... 40 33 193.8
Nov. 27, 1990 [DE] Germany .......... 40 37 636.2

[51] Int. Cl.$^6$ ............. A01N 43/16; C07D 309/34
[52] U.S. Cl. .................. 504/100; 504/294; 504/344; 549/426; 549/491; 549/496; 564/256
[58] Field of Search .......... 504/100, 292, 293, 294, 504/344; 549/426, 496, 491; 564/256

[56] References Cited

U.S. PATENT DOCUMENTS

| | | | |
|---|---|---|---|
| 4,249,937 | 2/1981 | Iwataki et al. | 71/97 |
| 4,440,566 | 4/1984 | Luo | 71/98 |
| 4,604,132 | 8/1986 | Conway et al. | 71/90 |
| 4,717,418 | 1/1988 | Warner et al. | 71/98 |
| 4,789,396 | 12/1988 | Arai et al. | 71/94 |
| 4,880,456 | 11/1989 | Kolassa et al. | 71/88 |
| 5,022,914 | 6/1991 | Kast et al. | 71/88 |
| 5,041,679 | 8/1991 | Hiratsuka et al. | 568/43 |

FOREIGN PATENT DOCUMENTS 0125094 11/1984 European Pat. Off.
0218233 4/1987 European Pat. Off.

(List continued on next page.)

Primary Examiner—Mary C. Lee
Assistant Examiner—Jacqueline Haley
Attorney, Agent, or Firm—Keil & Weinkauf

[57] ABSTRACT

Unsaturated cyclohexenone oxime ethers I

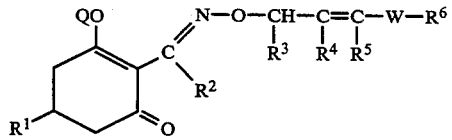

(Q=H, alkylcarbonyl, benzoyl, alkali metal or alkaline earth metal ion, substituted or unsubstituted ammonium ion, phosphonium ion, sulfonium ion, sulfoxonium ion, an equivalent of a transition metal cation; W=—C≡C— or —CH=CH—;
$R^1$=substituted or unsubstituted cycloalkyl, cycloalkenyl or 6-membered heterocyclic group which has 1–2 oxygen and/or sulfur atoms and can be saturated or partially unsaturated; substituted or unsubstituted 5-membered saturated heterocycle with 1–2 oxygen and/or sulfur atoms; substituted or unsubstituted 5-membered heteroaromatic group with 1–2 nitrogen atoms and/or 1 oxygen or sulfur atom; substituted or unsubstituted phenyl, pyridyl or $R^9$—X-substituted alkyl with X=O, S, —SO—, —SO$_2$— and
$R^9$=alkyl, phenyl, 5/6-membered hetaryl with 1–3 hetero atoms;
$R^2$=alkyl;
$R^3$=H, alkyl;
$R^4$=H, halogen, alkyl;
$R^5$=H, alkyl;
or $R^3+R^4$, $R^3+R^5$ or $R^4+R^5$ together form $C_2$–$C_4$-alkylene or $C_2$–$C_4$-alkenylene;
$R^6$=H, alkyl, unsubstituted or phenyl-substituted haloalkyl, alkenyl, alkoxyalkyl, alkylthioalkyl, substituted or unsubstituted cycloalkyl or cycloalkenyl; substituted or unsubstituted phenyl or pyridyl) are suitable as herbicides.

3 Claims, No Drawings

FOREIGN PATENT DOCUMENTS

| | | |
|---|---|---|
| 0230235 | 7/1987 | European Pat. Off. . |
| 0238021 | 9/1987 | European Pat. Off. . |
| 0253537 | 1/1988 | European Pat. Off. . |
| 0254514 | 1/1988 | European Pat. Off. . |
| 0080301 | 8/1988 | European Pat. Off. . |
| 0323915 | 7/1989 | European Pat. Off. . |
| 0341048 | 11/1989 | European Pat. Off. : |
| 3838309 | 5/1990 | Germany . |
| 1153637 | 12/1987 | Japan . |
| 1157947 | 12/1987 | Japan . |
| 1157948 | 12/1987 | Japan . |
| 1157949 | 12/1987 | Japan . |
| 1157950 | 12/1987 | Japan . |
| 1168664 | 12/1987 | Japan . |
| 1180869 | 1/1988 | Japan . |
| 1180870 | 1/1988 | Japan . |
| 1180871 | 1/1988 | Japan . |
| 1006255 | 1/1989 | Japan . |
| 1013064 | 1/1989 | Japan . |
| 1013066 | 1/1989 | Japan . |
| 1013068 | 1/1989 | Japan . |
| 1016759 | 1/1989 | Japan . |
| 1029355 | 1/1989 | Japan . |
| 1031756 | 2/1989 | Japan . |

UNSATURATED CYCLOHEXENONE OXIME ETHERS AND HERBICIDAL COMPOSITIONS THEREOF

This is a division application Ser. No. 776,044, filed Oct. 16, 1991, now abandoned.

The present invention relates to novel unsaturated cyclohexenone oxime ethers of the formula I

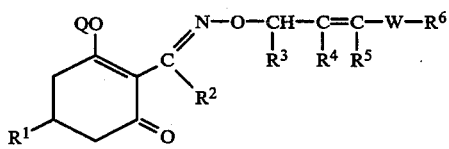

where

Q is hydrogen, $C_1$–$C_4$-alkylcarbonyl, benzoyl, an alkali metal or alkaline earth metal ion, an ammonium ion whose nitrogen can carry from one to four $C_1$–$C_4$-alkyl, phenyl and/or benzyl substituents, or a phosphonium, sulfonium or sulfoxonium ion or an equivalent of a transition metal cation;

W is —C≡C— or —CH=CH—;

$R^1$ is $C_3$–$C_7$-cycloalkyl or $C_5$–$C_7$-cycloalkenyl, a 6-membered heterocyclic group which has one or two non-adjacent oxygen and/or sulfur atoms and can be saturated or partially unsaturated, it also being possible for the cyclic groups to carry one to three of the following: hydroxyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio; a 5-membered saturated heterocycle which has one or two oxygen and/or sulfur atoms as hetero atoms and can also carry one to three of the following: $C_1$–$C_4$-alkyl, partially or completely halogenated $C_1$–$C_4$-alkyl, $C_1$–$C_4$-alkoxy or $C_1$–$C_4$-alkylthio; a 5-membered heteroaromatic group which has one or two nitrogen atoms and/or one oxygen or sulfur atom and can also carry one to three of the following: cyano, halogen, $C_1$–$C_4$-alkyl, partially or completely halogenated $C_1$–$C_4$-alkyl, $C_2$–$C_6$-alkenyl, partially or completely halogenated $C_2$–$C_6$-alkenyl, $C_1$–$C_4$-alkoxy, $C_1$–$C_4$-alkylthio, $C_2$–$C_6$-alkenyloxy or $C_1$–$C_4$-alkoxy-$C_1$–$C_4$-alkyl; phenyl or pyridyl, or $C_1$–$C_6$-alkyl which is substituted by $R^7$—X— where X is oxygen, sulfur, —SO— or —$SO_2$— and $R^7$ is $C_1$–$C_4$-alkyl, phenyl or 5- or 6-membered hetaryl with one to three hetero atoms selected from the group comprising one oxygen or sulfur atom and three nitrogen atoms, excepting compounds with three adjacent hetero atoms in the heterocycle, and where the aromatic or heteroaromatic moiety of these groups can also carry one to three of the following: nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_1$–$C_4$-alkoxy-$C_1$–$C_4$-alkyl, $C_1$–$C_4$-alkylthio-$C_1$–$C_4$-alkyl, $C_3$–$C_6$-alkenyloxy, $C_3$–$C_6$-alkynyloxy or —$NR^8R^9$ where $R^8$ is hydrogen, $C_1$–$C_4$-alkyl, $C_3$–$C_4$-alkenyl or $C_3$–$C_4$-alkynyl and $R^9$ is hydrogen, $C_1$–$C_4$-alkyl, $C_3$–$C_4$-alkenyl, $C_3$–$C_4$-alkynyl, $C_1$–$C_6$-alkylcarbonyl or benzoyl which can also carry one to three of the following: nitro, cyano, halogen, $C_1$–$C_4$-alkyl, partially or completely halogenated $C_1$–$C_4$-alkyl, $C_1$–$C_4$-alkoxy or $C_1$–$C_4$-alkylthio;

$R^2$ is $C_1$–$C_6$-alkyl;

$R^3$ is hydrogen or $C_1$–$C_6$-alkyl;

$R^4$ is hydrogen, halogen or $C_1$–$C_6$-alkyl;

$R^5$ is hydrogen or $C_1$–$C_6$-alkyl;

or $R^3$ and $R^4$, $R^3$ and $R^5$ or $R^4$ and $R^5$ together form $C_2$–$C_4$-alkylene or $C_2$–$C_4$-alkenylene;

$R^6$ is hydrogen, $C_1$–$C_6$-alkyl, partially or completely halogenated $C_1$–$C_4$-alkyl which can also carry a phenyl radical, or $C_2$–$C_6$-alkenyl, $C_1$–$C_4$-alkoxy-$C_1$–$C_4$-alkyl, $C_1$–$C_4$-alkylthio-$C_1$–$C_4$-alkyl, $C_3$–$C_7$-cycloalkyl or $C_5$–$C_7$-cycloalkenyl, both of which can also carry one to three of the following: hydroxyl, $C_1$–$C_4$-alkyl, partially or completely halogenated $C_1$–$C_4$-alkyl, $C_1$–$C_4$-alkoxy, $C_1$–$C_4$-alkoxy-$C_1$–$C_4$-alkyl or $C_1$–$C_4$-alkylthio-$C_1$–$C_4$-alkyl; phenyl or pyridyl, both of which can also carry one to three of the following: nitro, cyano, hydroxyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_1$–$C_4$-alkoxy-$C_1$–$C_4$-alkyl or $C_1$–$C_4$-alkylthio-$C_1$–$C_4$-alkyl.

The present invention also relates to herbicidal agents which contain these compounds as active substances.

The present invention also relates to hydroxylamines of the formula IIIb

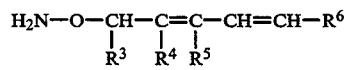

and phthalimides of the formula IX

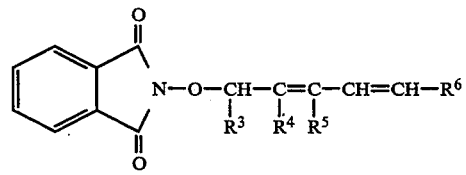

as intermediates.

Herbicidal cyclohexenone oxime ethers of the type of compounds I but which differ in the oxime ether moiety and/or in the substituent in position 5 of the cyclohexane-1,3-dione structure from compounds I are disclosed in the following:

a) U.S. Pat. No. 4,440,566 (haloalkenyl and benzyl ethers);
b) U.S. Pat. No. 4,249,937 (alkyl and alkenyl ethers);
c) EP-A 080 301, EP-A 238 021 and EP-A 125 094 (benzyl ethers and 2-butenyl ethers);
d) EP-A 218 233 (2-butenyl ethers);
e) DE-A 38 38 309 (4-phenylbutyl, 4-phenyl-2-butenyl and 4-phenyl-3-butenyl ethers);
f) EP-A 253 537, EP-A 323 915, EP-A 254 514, JP-A 1006 255, JP-A 1013 068, JP-A 1013 064, JP-A 1013 066, JP-A 1016 759, JP-A 1029 355, JP-A 1031 756, JP-A 1153 637, JP-A 1157 947, JP-A 1157 948, JP-A 1157 949, JP-A 1157 950, JP-A 1168 664, JP-A 1180 869, JP-A 1180 870 and JP-A 1180 871 (benzyl ethers and butenyl ethers).

However, there is a need for compounds which at lower application rates have a good herbicidal action against unwanted graminaceous plants but cause negligible damage to crop plants.

It is an object of the present invention to find novel substances with an improved herbicidal action.

We have found that this object is achieved by the cyclohexenone oxime ethers I defined in the first paragraph.

We have also found herbicidal agents which contain these substances.

The specific meanings of the variables in the novel compounds I are as follows:

Q is
  hydrogen;
  branched or unbranched $C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, 1-ethylhexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl;
  benzoyl;
  an alkali metal or alkaline earth metal ion such as sodium, potassium, calcium, magnesium and barium;
  an ammonium ion whose nitrogen can carry from one to four substituents selected from the group comprising four $C_1$–$C_4$-alkyl substituents such as methyl, ethyl, n-propyl, isopropyl, n-butyl and tert-butyl, two phenyl and two benzyl substituents, especially a diisopropylammonium, tetramethylammonium, tetrabutylammonium and trimethylbenzylammonium ion;
  a phosphonium ion;
  a sulfonium ion, especially a trialkylsulfonium ion;
  a sulfoxonium ion;
  an equivalent of a transition metal cation, especially manganese, iron, copper and zinc;

W is
  —C≡C— or —CH=CH—;

$R^1$ is
  $C_3$–$C_7$-cycloalkyl such as cyclopropyl, cyclobutyl, cyclopentyl and cyclohexyl, $C_5$–$C_7$-cycloalkenyl such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 4-cycloheptenyl, or a 6-membered heterocyclic group which has one or two non-adjacent oxygen and/or sulfur atoms and can be saturated or partially unsaturated, such as 5,6-dihydropyran-3-yl, 5,6-dihyrothiopyran-3-yl, tetrahydropyran-3-yl, tetrahydropyran-4-yl, tetrahydrothiopyran-3-yl and 1,3-dioxepan-5-yl, where the cyclic groups can also carry one to three of the following: hydroxyl, halogen such as fluorine, chlorine, bromine and iodine, especially chlorine and bromine, $C_1$–$C_4$-alkyl such as methyl, ethyl, n-propyl, isopropyl, n-butyl and tert-butyl, especially methyl and isopropyl, partially or completely halogenated $C_1$–$C_4$-alkyl such as fluoromethyl, chloromethyl, bromomethyl, difluoromethyl, trifluoromethyl, trichloromethyl, 1-chloroethyl, pentafluoroethyl, 4-chloro-1-butyl and 2-chloro-1,1,2-trifluoroethyl, especially difluoromethyl and trifluoromethyl, $C_1$–$C_4$-alkoxy such as methoxy, ethoxy, n-propoxy, isopropoxy, n-butoxy and tert-butoxy, partially or completely halogenated $C_1$–$C_4$-alkoxy such as difluoromethoxy, trifluoromethoxy and 1,1,2,2-tetrafluoroethoxy, especially difluoromethoxy and trifluoromethoxy, or $C_1$–$C_4$-alkylthio such as methylthio, ethylthio, n-propylthio, isopropylthio, 1-methylpropylthio, 2-methylpropylthio, n-butylthio and tert-butylthio, especially methylthio; particularly preferred are 1-methylthiocyclopropyl, cyclohexyl, cyclohexenyl, 5,6-dihydropyran-3-yl, tetrahydropyran-3-yl, tetrahydropyran-4-yl, tetrahydrothiopyran-3-yl, 4-methylcyclohexyl, 3,4-dihydroxycyclohexyl, 3,4-dibromotetrahydropyran-3-yl, 2-isopropyl-1,3-dioxepan-5-yl;
  a 5-membered saturated heterocycle which has one or two oxygen and/or sulfur atoms as hetero atoms, eg. tetrahydrofuryl, 1,3-dioxolan-2-yl and 1,3-dithiolan-2-yl, and which can also carry one to three of the following: $C_1$–$C_4$-alkyl as mentioned above, especially methyl, partially or completely halogenated $C_1$–$C_4$-alkyl as mentioned above, especially trifluoromethyl, $C_1$–$C_4$-alkoxy as mentioned above, especially methoxy and ethoxy, or $C_1$–$C_4$-alkylthio as mentioned above, especially methylthio;
  a 5-membered heteroaromatic group which has one or two nitrogen atoms and/or one oxygen or sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, and which can also carry one to three of the following: cyano, halogen as mentioned above, especially fluorine and chlorine, $C_1$–$C_4$-alkyl as mentioned above, partially or completely halogenated $C_1$–$C_4$-alkyl as mentioned above, especially trifluoromethyl, $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; especially ethenyl, allyl and 1-methylethenyl, partially or completely halogenated $C_2$-$C_6$-alkenyl such as 3-chloropropenyl and 2,3,3-trichloropropenyl; $C_1$-$C_4$-alkoxy as mentioned above, especially methoxy and ethoxy, $C_1$-$C_4$-alkylthio as mentioned above, especially methylthio, $C_2$-$C_6$-alkenyloxy such as ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy and 1-ethyl-2-methyl-2-propenyloxy, preferably 2-propenyloxy, or $C_1$-$C_4$-alkoxy-$C_1$-$C_4$-alkyl such as methoxymethyl, methoxyethyl, ethoxymethyl, ethoxyethyl, especially methoxymethyl and ethoxymethyl;

phenyl or pyridyl, or $C_1$-$C_6$-alkyl which is substituted by $R^7$—X— where X is oxygen, sulfur, —SO— or —$SO_2$— and $R^7$ is $C_1$-$C_4$-alkyl, phenyl or 5- or 6-membered hetaryl with one to three hetero atoms selected from the group comprising one oxygen or sulfur atom and three nitrogen atoms, excepting compounds with three adjacent hetero atoms in the heterocycle, and where the aromatic or heteroaromatic moiety in these groups can also carry one to three of the following: nitro, cyano, halogen as mentioned above, especially fluorine and chlorine, $C_1$-$C_4$-alkyl as mentioned above, partially or completely halogenated $C_1$-$C_4$-alkyl as mentioned above, especially difluoromethyl and trifluoromethyl, $C_1$-$C_4$-alkoxy as mentioned above, especially methoxy and ethoxy, partially or completely halogenated $C_1$-$C_4$-alkoxy as mentioned above, especially difluoromethoxy and trifluoromethoxy, $C_1$-$C_4$-alkylthio as mentioned above, especially methylthio, $C_1$-$C_4$-alkoxy-$C_1$-$C_4$-alkyl as mentioned above, especially methoxymethyl and ethoxymethyl, $C_1$-$C_4$-alkylthio-$C_1$-$C_4$-alkyl as mentioned above, especially methylthiomethyl, $C_3$-$C_6$-alkenyloxy such as 2-propenyloxy and 2-butenyloxy, $C_3$-$C_6$-alkynyloxy such as 2-propynyloxy and 2-butynyloxy, or —$NR^8R^9$ where $R^8$ is hydrogen, $C_1$-$C_4$-alkyl as mentioned above, $C_3$-$C_4$-alkenyl such as 2-propenyl and 2-butenyl or $C_3$-$C_4$-alkynyl such as 2-propynyl and 2-butynyl and $R^9$ is hydrogen, $C_1$-$C_4$-alkyl as mentioned above, $C_3$-$C_4$-alkenyl as mentioned above, $C_3$-$C_4$-alkynyl as mentioned above, $C_1$-$C_6$-alkylcarbonyl as mentioned above, or benzoyl which can also carry one to three of the following: nitro, cyano, halogen as mentioned above, especially fluorine and chlorine, $C_1$-$C_4$-alkyl as mentioned above, partially or completely halogenated $C_1$-$C_4$-alkyl as mentioned above, especially trifluoromethyl, $C_1$-$C_4$-alkoxy as mentioned above, especially methoxy and ethoxy, or $C_1$-$C_4$-alkylthio as mentioned above, especially methylthio;

$R^2$ is
 branched or unbranched $C_1$-$C_6$-alkyl, especially $C_1$-$C_4$-alkyl as mentioned above;

$R^3$ is
 hydrogen or
 branched or unbranched $C_1$-$C_6$-alkyl, especially $C_1$-$C_4$-alkyl as mentioned above;

$R^4$ is
 hydrogen,
 halogen as mentioned above, especially fluorine and chlorine, or
 branched or unbranched $C_1$-$C_6$-alkyl, especially $C_1$-$C_4$-alkyl as mentioned above;

$R^5$ is
 hydrogen,
 branched or unbranched $C_1$-$C_6$-alkyl, especially $C_1$-$C_4$-alkyl as mentioned above; or
 $R^3$ and $R^4$, $R^4$ and $R^5$ or, preferably, $R^3$ and $R^5$ together form branched or unbranched $C_2$-$C_4$-alkylene or $C_2$-$C_4$-alkenylene such as ethylene, propylene, 2-methylpropylene, butylene, 2-propenylene and 2-butenylene, especially propylene, butylene and 2-butenylene;

$R^6$ is
 hydrogen;
 branched or unbranched $C_1$-$C_6$-alkyl, especially $C_1$-$C_4$-alkyl as mentioned above;

partially or completely halogenated $C_1$–$C_4$-alkyl as mentioned above, especially difluoromethyl and trifluoromethyl, it also being possible for the alkyl to carry a phenyl radical; 2,2,2-trifluoro-1-phenylethyl is preferred;

$C_2$–$C_6$-alkenyl as mentioned above, especially ethenyl and 2-propenyl;

$C_1$–$C_4$-alkoxy-$C_1$–$C_4$-alkyl as mentioned above, especially methoxymethyl, methoxyethyl, ethoxymethyl and ethoxyethyl;

$C_1$–$C_4$-alkylthio-$C_1$–$C_4$-alkyl such as methylthiomethyl, methylthioethyl, ethylthiomethyl and ethylthioethyl;

$C_3$–$C_7$-cycloalkyl or $C_5$–$C_7$-cycloalkenyl as mentioned above, especially cyclopentyl, cyclohexyl and cyclohexenyl, which can also carry one to three of the following: hydroxyl, $C_1$–$C_4$-alkyl as mentioned above, partially or completely halogenated $C_1$–$C_4$-alkyl as mentioned above, especially trifluoromethyl, $C_1$–$C_4$-alkoxy as mentioned above, especially methoxy and ethoxy, $C_1$–$C_4$-alkoxy-$C_1$–$C_4$-alkyl as mentioned above, especially methoxymethyl and ethoxymethyl or $C_1$–$C_4$-alkylthio-$C_1$–$C_4$-alkyl as mentioned above, especially methylthiomethyl;

phenyl or pyridyl, both of which can also carry one to three of the following: nitro, cyano, hydroxyl, halogen as mentioned above, especially fluorine and chlorine, $C_1$–$C_4$-alkyl as mentioned above, partially or completely halogenated $C_1$–$C_4$-alkyl as mentioned above, especially trifluoromethyl, $C_1$–$C_4$-alkoxy as mentioned above, especially methoxy and ethoxy, partially or completely halogenated $C_1$–$C_4$-alkoxy as mentioned above, especially trifluoromethoxy, $C_1$–$C_4$-alkylthio as mentioned above, especially methylthio, $C_1$–$C_4$-alkoxy-$C_1$–$C_4$-alkyl as mentioned above, especially methoxymethyl and ethoxymethyl or $C_1$–$C_4$-alkylthio-$C_1$–$C_4$-alkyl as mentioned above, especially methylthiomethyl; phenyl, pyridyl, 4-fluorophenyl and 4-chlorophenyl are particularly preferred.

Examples of possible compounds I are listed in Tables A and B which follow:

TABLE A

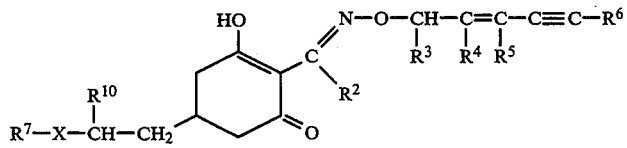

(I)  ($R^1$ = —$CH_2$—$CH(R^{10})$—X—$R^7$ with $R^{10}$ = H; $CH_3$)

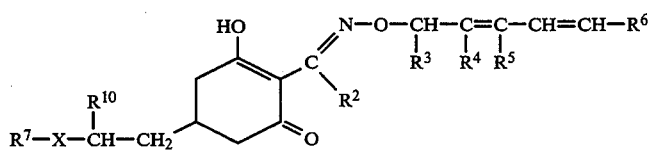

| $R^{10}$ | X | $R^7$ | $R^2$ | $R^3$ | $R^5$ | $R^4$ | $R^6$ |
|---|---|---|---|---|---|---|---|
| H | S | 4-$CF_3$-phenyl | Ethyl | H | H | F | 4-F-phenyl |
| H | S | 4-F-phenyl | Propyl | $CH_3$ | H | F | 4-Cl-phenyl |
| $CH_3$ | S | 4-($CF_3$—O—)phenyl | Ethyl | H | H | H | Phenyl |
| $CH_3$ | S | 4-Br-phenyl | Propyl | $CH_3$ | H | H | Pyridin-3-yl |
| H | S | 4-$CHF_2$-phenyl | Ethyl | —$(CH_2)_3$— | | H | 4-F-phenyl |
| H | S | 4-($CHF_2$—O—)phenyl | Propyl | H | $CH_3$ | $CH_3$ | 3-Cl-phenyl |
| $CH_3$ | S | 4-($CHF_2$—$CF_2$—O—)phenyl | Ethyl | H | H | F | 3-$CF_3$-phenyl |
| $CH_3$ | S | 2-F-4-$CF_3$-phenyl | Propyl | $C_2H_5$ | H | F | 4-$CH_3$—O—phenyl |
| H | S | 5-$CF_3$-pyridin-2-yl | Ethyl | $CH_3$ | $CH_3$ | H | tert.-Butyl |
| H | S | 5-$CHF_2$-pyridin-2-yl | Propyl | —$(CH_2)_3$— | | F | 2,2,2-$F_3$-1-phenylethyl |
| $CH_3$ | S | 5-$CF_3$-pyridin-2-yl | Ethyl | n-$C_3H_7$ | H | F | 3,3,3-$F_3$-prop-2-yl |
| $CH_3$ | S | 5-F-pyridin-2-yl | Propyl | H | $CH_3$ | F | 2-$CH_3O$—prop-2-yl |
| H | S | 5-($CF_3$—O—)pyridin-2-yl | Ethyl | $CH_3$ | H | H | Cyclohexyl |
| H | S | 5-($CHF_2$—O—)-pyridin-2-yl | Propyl | $CH_3$ | H | Et | Cyclopentyl |
| $CH_3$ | S | 4-Cl-phenyl | Ethyl | —$(CH_2)_3$— | | $CH_3$ | Propen-2-yl |
| $CH_3$ | S | 5-Br-pyridin-2-yl | Propyl | H | H | F | 3-$CF_3$-phenyl |
| $CH_3$ | S | 4-$CF_3$-phenyl | Ethyl | $C_2H_5$ | H | F | H |
| H | S | 4-$CF_3$-phenyl | Ethyl | H | H | F | 3-$CH_3$-pent-3-yl |
| H | S | 4-F-phenyl | Propyl | $CH_3$ | H | F | Cyclohex-2-en-1-yl |
| $CH_3$ | S | 4-($CF_3$—O—)phenyl | Ethyl | H | H | H | Pyridin-2-yl |
| $CH_3$ | S | 4-Br-phenyl | Propyl | $CH_3$ | H | H | Trimethylsilyl |
| H | S | 4-$CHF_2$-phenyl | Ethyl | —$(CH_2)_3$— | | H | Isopropyl |
| H | S | 4-($CHF_2$—O—)phenyl | Propyl | H | $CH_3$ | $CH_3$ | n-Hexyl |
| $CH_3$ | S | 4-($CHF_2$—$CF_2$—O—)phenyl | Ethyl | H | H | F | 4-$CH_3O$—phenyl |
| $CH_3$ | S | 2-F-4-$CF_3$-phenyl | Propyl | $C_2H_5$ | H | F | 4-$CF_3$-phenyl |
| H | S | 5-$CF_3$-pyridin-2-yl | Ethyl | $CH_3$ | $CH_3$ | H | 3,4-$Cl_2$-phenyl |
| H | S | 5-$CHF_2$-pyridin-2-yl | Propyl | —$(CH_2)_3$— | | F | 4-Cl-phenyl |
| $CH_3$ | S | 5-$CF_3$-pyridin-2-yl | Ethyl | n-$C_3H_7$ | H | F | 3-F-phenyl |
| $CH_3$ | S | 5-F-pyridin-2-yl | Propyl | H | $CH_3$ | F | Phenyl |
| H | S | 5-($CF_3$—O—)pyridin-2-yl | Ethyl | $CH_3$ | H | H | H |
| H | S | 5-($CHF_2$—O—)-pyridin-2-yl | Propyl | $CH_3$ | H | Et | tert.-Butyl |
| $CH_3$ | S | 4-Cl-phenyl | Ethyl | —$(CH_2)_3$— | | $CH_3$ | 1,1,1-$F_3$-prop-2-yl |
| $CH_3$ | S | 5-Br-pyridin-2-yl | Propyl | H | H | F | 2-$CH_2Cl$-but-2-yl |
| $CH_3$ | S | 4-$CF_3$-phenyl | Ethyl | $C_2H_5$ | H | F | 4-F-phenyl |
| H | SO | 4-$CF_3$-phenyl | Ethyl | H | H | F | 4-F-phenyl |

TABLE A-continued (I)  ($R^1$ = —$CH_2$—$CH(R^{10})$—X—$R^7$ with $R^{10}$ = H; $CH_3$)

| $R^{10}$ | X | $R^7$ | $R^2$ | $R^3$ | $R^5$ | $R^4$ | $R^6$ |
|---|---|---|---|---|---|---|---|
| H | SO | 4-F-phenyl | Propyl | $CH_3$ | H | F | 4-Cl-phenyl |
| $CH_3$ | SO | 4-($CF_3$—O—)phenyl | Ethyl | H | H | H | Phenyl |
| $CH_3$ | SO | 4-Br-phenyl | Propyl | $CH_3$ | H | H | Pyridin-3-yl |
| H | SO | 4-$CHF_2$-phenyl | Ethyl | —$(CH_2)_3$— | | H | 4-F-phenyl |
| H | SO | 4-($CHF_2$—O—)phenyl | Propyl | H | $CH_3$ | $CH_3$ | 3-Cl-phenyl |
| $CH_3$ | SO | 4-($CHF_2$—$CF_2$—O—)phenyl | Ethyl | H | H | F | 3-$CF_3$-phenyl |
| $CH_3$ | SO | 2-F-4-$CF_3$-phenyl | Propyl | $C_2H_5$ | H | F | 3-$CH_3O$—phenyl |
| H | SO | 5-$CF_3$-pyridin-2-yl | Ethyl | $CH_3$ | $CH_3$ | H | tert.-Butyl |
| H | SO | 5-$CHF_2$-pyridin-2-yl | Propyl | —$(CH_2)_3$— | | F | 2,2,2-$F_3$-1-phenylethyl |
| $CH_3$ | SO | 5-$CF_3$-pyridin-2-yl | Ethyl | n-$C_3H_7$ | H | F | 3,3,3-$F_3$-prop-2-yl |
| $CH_3$ | SO | 5-F-pyridin-2-yl | Propyl | H | $CH_3$ | F | 2-$CH_3O$—prop-2-yl |
| H | SO | 5-($CF_3$—O—)pyridin-2-yl | Ethyl | $CH_3$ | H | H | Cyclohexyl |
| H | SO | 5-($CHF_2$—O—)-pyridin-2-yl | Propyl | $CH_3$ | H | Et | Cyclopentyl |
| $CH_3$ | SO | 4-Cl-phenyl | Ethyl | —$(CH_2)_3$— | | $CH_3$ | Propen-2-yl |
| $CH_3$ | SO | 5-Br-pyridin-2-yl | Propyl | H | H | F | 3-$CF_3$-phenyl |
| $CH_3$ | SO | 4-$CF_3$-phenyl | Ethyl | $C_2H_5$ | H | F | H |
| H | $SO_2$ | 4-$CF_3$-phenyl | Ethyl | H | H | F | 3-$CH_3$-pent-3-yl |
| H | $SO_2$ | 4-F-phenyl | Propyl | $CH_3$ | H | F | Cyclohex-2-en-1-yl |
| $CH_3$ | $SO_2$ | 4-($CF_3$—O—)phenyl | Ethyl | H | H | H | Pyridin-2-yl |
| $CH_3$ | $SO_2$ | 4-Br-phenyl | Propyl | $CH_3$ | H | H | Trimethylsilyl |
| H | $SO_2$ | 4-$CHF_2$-phenyl | Ethyl | —$(CH_2)_3$— | | H | Isopropyl |
| H | $SO_2$ | 4-($CHF_2$—O—)phenyl | Propyl | H | $CH_3$ | $CH_3$ | n-Hexyl |
| $CH_3$ | $SO_2$ | 4-($CHF_2$—$CF_2$—O—)phenyl | Ethyl | H | H | F | 4-$CH_3O$—phenyl |
| $CH_3$ | $SO_2$ | 2-F-4-$CF_3$-phenyl | Propyl | $C_2H_5$ | H | F | 4-$CF_3$-phenyl |
| H | $SO_2$ | 5-$CF_3$-pyridin-2-yl | Ethyl | $CH_3$ | $CH_3$ | H | 3,4-$Cl_2$-phenyl |
| H | $SO_2$ | 5-$CHF_2$-pyridin-2-yl | Propyl | —$(CH_2)_3$— | | F | 4-Cl-phenyl |
| $CH_3$ | $SO_2$ | 5-$CF_3$-pyridin-2-yl | Ethyl | n-$C_3H_7$ | H | F | 3-F-phenyl |
| $CH_3$ | $SO_2$ | 5-F-pyridin-2-yl | Propyl | H | $CH_3$ | F | Phenyl |
| H | $SO_2$ | 5-($CF_3$—O—)pyridin-2-yl | Ethyl | $CH_3$ | H | H | H |
| H | $SO_2$ | 5-($CHF_2$—O—)-pyridin-2-yl | Propyl | $CH_3$ | H | Et | tert.-Butyl |
| $CH_3$ | $SO_2$ | 4-Cl-phenyl | Ethyl | —$(CH_2)_3$— | | $CH_3$ | 1,1,1-$F_3$-prop-2-yl |
| $CH_3$ | $SO_2$ | 5-Br-pyridin-2-yl | Propyl | H | H | F | 2-$CH_2Cl$-but-2-yl |
| $CH_3$ | $SO_2$ | 4-$CF_3$-phenyl | Ethyl | $C_2H_5$ | H | F | 4-F-phenyl |
| H | S | Ethyl | Ethyl | H | H | F | 4-F-phenyl |
| H | S | Ethyl | Propyl | $CH_3$ | H | F | 4-Cl-phenyl |
| $CH_3$ | S | Ethyl | Ethyl | H | H | H | Phenyl |
| $CH_3$ | S | Ethyl | Propyl | $CH_3$ | H | H | Pyridin-3-yl |
| H | S | Ethyl | Ethyl | —$(CH_2)_3$— | | H | 4-F-phenyl |
| H | S | Ethyl | Propyl | H | $CH_3$ | $CH_3$ | 3-Cl-phenyl |
| $CH_3$ | S | Ethyl | Ethyl | H | H | F | 3-$CF_3$-phenyl |
| $CH_3$ | S | Ethyl | Propyl | $C_2H_5$ | H | F | 4-$CH_3O$—phenyl |
| H | S | Ethyl | Ethyl | $CH_3$ | $CH_3$ | H | tert.-Butyl |
| H | S | Ethyl | Propyl | —$(CH_2)_3$— | | F | 2,2,2-$F_3$-1-phenylethyl |
| $CH_3$ | S | Ethyl | Ethyl | Propyl | H | F | 1,1,1-$F_3$-prop-2-yl |
| $CH_3$ | S | Ethyl | Propyl | H | $CH_3$ | F | 2-$CH_3O$—prop-2-yl |
| H | S | Ethyl | Ethyl | $CH_3$ | H | H | Cyclohexyl |
| H | S | Ethyl | Propyl | $CH_3$ | H | Et | Cyclopentyl |
| $CH_3$ | S | Ethyl | Ethyl | —$(CH_2)_3$— | | $CH_3$ | Propen-2-yl |
| $CH_3$ | S | Ethyl | Propyl | H | H | F | 3-$CF_3$-phenyl |
| $CH_3$ | S | Ethyl | Ethyl | $C_2H_5$ | H | F | H |

TABLE B

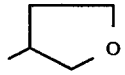

I (W = —C≡C—)

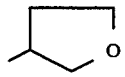

I (W = —CH=CH—)

| $R^1$ | $R^2$ | $R^3$ | $R^5$ | $R^4$ | $R^6$ |
|---|---|---|---|---|---|
|  | $CH_2CH_3$ | H | H | F | Phenyl |
| 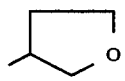 | $(CH_2)_2CH_3$ | $CH_3$ | H | F | tert.-Butyl |
|  | $CH_2CH_3$ | $C_2H_5$ | H | H | n-Hexyl |
|  | $(CH_2)_2CH_3$ | H | $CH_3$ | F | 4-F-phenyl |
|  | $CH_2CH_3$ | —$(CH_2)_3$— | | F | 2,2,2-$F_3$-1-phenylethyl |
|  | $(CH_2)_2CH_3$ | $CH_3$ | $CH_3$ | H | 1-$CH_3O$-eth-1-yl |
|  | $CH_2CH_3$ | n-$C_3H_7$ | H | F | Pyridin-3-yl |
|  | $(CH_2)_2CH_3$ | H | H | F | Cyclohexyl |
|  | $CH_2CH_3$ | —$(CH_2)_3$— | | H | 4-Cl-phenyl |
|  | $(CH_2)_2CH_3$ | H | $CH_3$ | F | 3-$CH_3$-pent-3-yl |
|  | $CH_2CH_3$ | H | H | H | Cyclohex-2-en-1-yl |
|  | $(CH_2)_2CH_3$ | $CH_3$ | $CH_3$ | F | Phenyl |
|  | $CH_2CH_3$ | H | H | F | Phenyl |

TABLE B-continued

Structure I (W = —C≡C—):
HO-C(=cyclohexenone with R¹)-C(R²)=N—O—CH(R³)—C(R⁴)=C(R⁵)—C≡C—R⁶

Structure I (W = —CH=CH—):
HO-C(=cyclohexenone with R¹)-C(R²)=N—O—CH(R³)—C(R⁴)=C(R⁵)—CH=CH—R⁶

| R¹ | R² | R³ | R⁵ | R⁴ | R⁶ |
|---|---|---|---|---|---|
| tetrahydrothiophen-3-yl | (CH₂)₂CH₃ | CH₃ | H | F | tert.-Butyl |
| tetrahydrothiophen-3-yl | CH₂CH₃ | C₂H₅ | H | H | n-Hexyl |
| tetrahydrofuran-3-yl | (CH₂)₂CH₃ | H | CH₃ | F | p-F-phenyl |
| tetrahydrothiophen-3-yl | CH₂CH₃ | —(CH₂)₃— | | F | 2,2,2-F₃-1-phenylethyl |
| tetrahydrothiophen-3-yl | (CH₂)₂CH₃ | CH₃ | CH₃ | H | 1-CH₃O-eth-1-yl |
| tetrahydrothiophen-3-yl | CH₂CH₃ | n-C₃H₇ | H | F | Pyridin-3-yl |
| tetrahydrothiophen-3-yl | (CH₂)₂CH₃ | H | H | F | Cyclohexyl |
| tetrahydrothiophen-3-yl | CH₂CH₃ | —(CH₂)₃— | | H | 4-Cl-phenyl |
| tetrahydrothiophen-3-yl | (CH₂)₂CH₃ | H | CH₃ | F | 3-CH₃-pent-3-yl |
| tetrahydrothiophen-3-yl | CH₂CH₃ | H | H | H | Cyclohex-2-en-1-yl |
| tetrahydrothiophen-3-yl | (CH₂)₂CH₃ | CH₃ | CH₃ | F | Phenyl |
| 1,3-dioxolan-4-yl | CH₂CH₃ | CH₃ | CH₃ | F | 1-Cl-tert.-butyl |
| 1,3-dioxolan-4-yl | (CH₂)₂CH₃ | CH₃ | H | F | Cyclopentyl |

TABLE B-continued
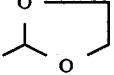
I (W = —C≡C—)
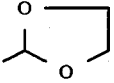
I (W = —CH=CH—)
| R¹ | R² | R³ | R⁵ | R⁴ | R⁶ |
|---|---|---|---|---|---|
| 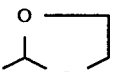 | CH₂CH₃ | H | H | F | Phenyl |
| 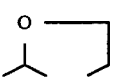 | (CH₂)₂CH₃ | CH₃ | H | F | tert.-Butyl |
| 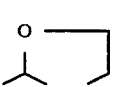 | CH₂CH₃ | C₂H₅ | H | H | n-Hexyl |
| 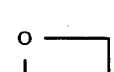 | (CH₂)₂CH₃ | H | CH₃ | F | p-F-phenyl |
| 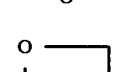 | CH₂CH₃ | —(CH₂)₃— | | F | 2,2,2-F₃-1-phenylethyl |
| 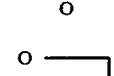 | (CH₂)₂CH₃ | CH₃ | CH₃ | H | 1-CH₃O-eth-1-yl |
| 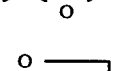 | CH₂CH₃ | n-C₃H₇ | H | F | Pyridin-3-yl |
| 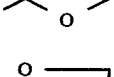 | (CH₂)₂CH₃ | H | H | F | Cyclohexyl |
| 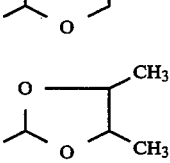 | CH₂CH₃ | —(CH₂)₃— | | H | p-Cl-phenyl |
| 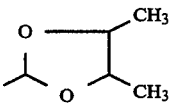 | (CH₂)₂CH₃ | H | CH₃ | F | 3-CH₃-pent-3-yl |
|  | CH₂CH₃ | CH₃ | CH₃ | F | Cyclohex-2-en-1-yl |
|  | (CH₂)₂CH₃ | H | H | H | Phenyl |

TABLE B-continued $$\text{Structure I (W = -C≡C-)}$$ with HO, N-O-CH(R³)-C(R⁴)=C(R⁵)-C≡C-R⁶ substitution on cyclohexanone ring bearing R¹ and R²

$$\text{Structure I (W = -CH=CH-)}$$ with HO, N-O-CH(R³)-C(R⁴)=C(R⁵)-CH=CH-R⁶ substitution on cyclohexanone ring bearing R¹ and R²

| R¹ | R² | R³ | R⁵ | R⁴ | R⁶ |
|---|---|---|---|---|---|
| 2-isopropyl-1,3-dioxolan-4-yl (4,5-diMe) | CH₂CH₃ | C₂H₅ | CH₃ | F | 1-Cl-tert.-Butyl |
| 2-isopropyl-1,3-dioxolan-4-yl (4,5-diMe) | (CH₂)₂CH₃ | H | H | F | Phenyl |
| 2-isopropyl-1,3-dioxolan-4-yl (4,5-diMe) | CH₂CH₃ | CH₃ | H | F | tert.-Butyl |
| 2-isopropyl-1,3-dioxolan-4-yl (4,5-diMe) | (CH₂)₂CH₃ | C₂H₅ | H | H | n-Hexyl |
| 2-isopropyl-1,3-dioxolan-4-yl (4,5-diMe) | CH₂CH₃ | H | CH₃ | F | p-F-phenyl |
| 2-isopropyl-1,3-dioxolan-4-yl (4,5-diMe) | (CH₂)₂CH₃ | —(CH₂)₃— |  | F | 1,1,1-F₃-2-phenylethyl |
| 2-isopropyl-1,3-dioxolan-4-yl (4,5-diMe) | CH₂CH₃ | CH₃ | CH₃ | H | 1-CH₃O-eth-1-yl |
| 2-isopropyl-1,3-dioxolan-4-yl (4,5-diMe) | (CH₂)₂CH₃ | n-C₃H₇ | H | F | Pyridin-3-yl |
| 2-isopropyl-1,3-dioxolan-4-yl (4,5-diMe) | CH₂CH₃ | H | H | F | Cyclohexyl |
| 2-isopropyl-1,3-dioxolan-4-yl (4,5-diMe) | (CH₂)₂CH₃ | —(CH₂)₃— |  | F | 4-Cl-phenyl |
| 2-isopropyl-1,3-dithiolan-4-yl | CH₂CH₃ | H | CH₃ | F | 3-CH₃-pent-3-yl |

TABLE B-continued

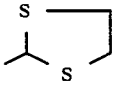

I (W = —C≡C—)

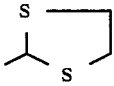

I (W = —CH=CH—)

| R[1] | R[2] | R[3] | R[5] | R[4] | R[6] |
|---|---|---|---|---|---|
| 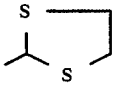 | (CH$_2$)$_2$CH$_3$ | H | H | H | Cyclohex-2-en-1-yl |
| 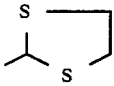 | CH$_2$CH$_3$ | CH$_3$ | CH$_3$ | F | Phenyl |
| 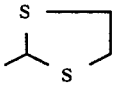 | (CH$_2$)$_2$CH$_3$ | H | H | F | Phenyl |
| 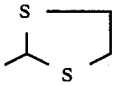 | CH$_2$CH$_3$ | CH$_3$ | H | F | tert.-Butyl |
| 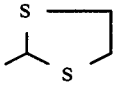 | (CH$_2$)$_2$CH$_3$ | C$_2$H$_5$ | H | H | n-Hexyl |
| 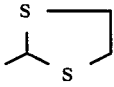 | CH$_2$CH$_3$ | H | CH$_3$ | F | 4-F-phenyl |
| 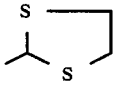 | (CH$_2$)$_2$CH$_3$ | —(CH$_2$)$_3$— | | F | 2,2,2-F$_3$-1-phenylethyl |
| 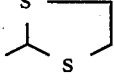 | CH$_2$CH$_3$ | CH$_3$ | CH$_3$ | H | 1-CH$_3$O-eth-1-yl |
| 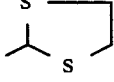 | (CH$_2$)$_2$CH$_3$ | n-C$_3$H$_7$ | H | F | Pyridin-3-yl |
| 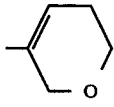 | CH$_2$CH$_3$ | H | H | CH$_3$ | Cyclohexyl |
|  | (CH$_2$)$_2$CH$_3$ | —(CH$_2$)$_3$— | | H | 4-Cl-phenyl |
|  | CH$_2$CH$_3$ | H | CH$_3$ | F | 3-CH$_3$-pent-3-yl |

TABLE B-continued $$\text{Structure I (W = -C\equiv C-): HO-cyclohexenone with C(R^2)=N-O-CH(R^3)-C(R^4)=C(R^5)-C\equiv C-R^6, with R^1 substituent}$$

$$\text{Structure I (W = -CH=CH-): HO-cyclohexenone with C(R^2)=N-O-CH(R^3)-C(R^4)=C(R^5)-CH=CH-R^6, with R^1 substituent}$$

| $R^1$ | $R^2$ | $R^3$ | $R^5$ | $R^4$ | $R^6$ |
|---|---|---|---|---|---|
| dihydropyranyl | $(CH_2)_2CH_3$ | H | H | $CH_3$ | Cyclohex-2-en-1-yl |
| dihydropyranyl | $CH_2CH_3$ | $CH_3$ | $CH_3$ | F | Phenyl |
| dihydropyranyl | $(CH_2)_2CH_3$ | $C_2H_5$ | $CH_3$ | F | 1-Cl-tert.-butyl |
| dihydropyranyl | $CH_2CH_3$ | H | H | F | Phenyl |
| dihydropyranyl | $(CH_2)_2CH_3$ | $CH_3$ | H | F | tert.-Butyl |
| dihydropyranyl | $CH_2CH_3$ | $C_2H_5$ | H | H | n-Hexyl |
| dihydropyranyl | $(CH_2)_2CH_3$ | H | $CH_3$ | F | 4-F-phenyl |
| dihydropyranyl | $CH_2CH_3$ | $-(CH_2)_3-$ | | F | 2,2,2-$F_3$-1-phenylethyl |
| dihydropyranyl | $(CH_2)_2CH_3$ | $CH_3$ | $CH_3$ | H | 1-$CH_3O$-eth-1-yl |
| dihydropyranyl | $CH_2CH_3$ | n-$C_3H_5$ | H | F | Pyridin-3-yl |

TABLE B-continued

Structure for I (W = —C≡C—): cyclohexenone with HO, R¹, and C(R²)=N—O—CH(R³)—C(R⁴)=C(R⁵)—C≡C—R⁶

Structure for I (W = —CH=CH—): cyclohexenone with HO, R¹, and C(R²)=N—O—CH(R³)—C(R⁴)=C(R⁵)—CH=CH—R⁶

| R¹ | R² | R³ | R⁵ | R⁴ | R⁶ |
|---|---|---|---|---|---|
| 4-(dihydropyranyl) | (CH₂)₂CH₃ | H | H | F | Cyclohexyl |
| 4,4-dibromo-dihydropyranyl | CH₂CH₃ | —(CH₂)₃— | | H | 4-Cl-phenyl |
| 4,4-dibromo-dihydropyranyl | (CH₂)₂CH₃ | H | CH₃ | F | 3-CH₃-pent-3-yl |
| 4,4-dibromo-dihydropyranyl | CH₂CH₃ | H | H | H | Cyclohex-2-en-1-yl |
| 4,4-dibromo-dihydropyranyl | (CH₂)₂CH₃ | CH₃ | CH₃ | F | Phenyl |
| 4,4-dibromo-dihydropyranyl | CH₂CH₃ | C₂H₅ | CH₃ | F | Cyclopentyl |
| 4,4-dibromo-dihydropyranyl | (CH₂)₂CH₃ | H | H | F | Phenyl |
| 4,4-dibromo-dihydropyranyl | CH₂CH₃ | CH₃ | H | F | tert.-Butyl |
| 4,4-dibromo-dihydropyranyl | (CH₂)₂CH₃ | C₂H₅ | H | H | n-Hexyl |

TABLE B-continued

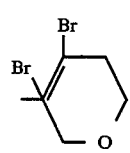

I (W = —C≡C—)

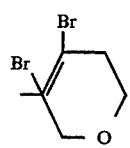

I (W = —CH=CH—)

| R$^1$ | R$^2$ | R$^3$ | R$^5$ | R$^4$ | R$^6$ |
|---|---|---|---|---|---|
| 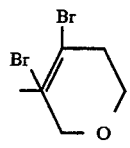 | CH$_2$CH$_3$ | H | CH$_3$ | F | p-F-phenyl |
| 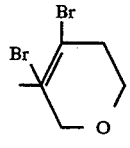 | (CH$_2$)$_2$CH$_3$ | —(CH$_2$)$_3$— | | F | 2,2,2-F$_3$-1-phenylethyl |
| 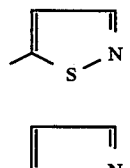 | CH$_2$CH$_3$ | CH$_3$ | CH$_3$ | H | 1-CH$_3$O-eth-1-yl |
| 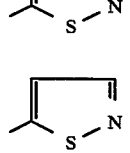 | (CH$_2$)$_2$CH$_3$ | n-C$_3$H$_7$ | H | F | Pyridin-3-yl |
| 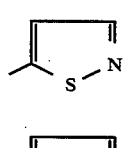 | CH$_2$CH$_3$ | H | F | H | Cyclohexyl |
| 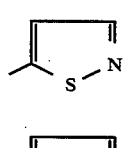 | (CH$_2$)$_2$CH$_3$ | —(CH$_2$)$_3$— | | H | 4-Cl-phenyl |
| 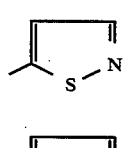 | CH$_2$CH$_3$ | H | CH$_3$ | F | 3-CH$_3$-pent-3-yl |
| 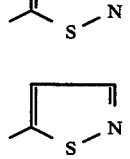 | (CH$_2$)$_2$CH$_3$ | H | H | CH$_3$ | Cyclohex-2-en-1-yl |
| 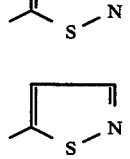 | CH$_2$CH$_3$ | CH$_3$ | CH$_3$ | CH$_3$ | Phenyl |
|  | (CH$_2$)$_2$CH$_3$ | H | H | F | Phenyl |

TABLE B-continued
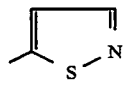
I (W = —C≡C—)
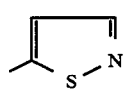
I (W = —CH=CH—)
| R¹ | R² | R³ | R⁵ | R⁴ | R⁶ |
|---|---|---|---|---|---|
| 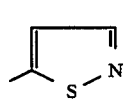 | CH₂CH₃ | CH₃ | H | F | tert.-Butyl |
|  | (CH₂)₂CH₃ | C₂H₅ | H | H | n-Hexyl |
|  | CH₂CH₃ | H | CH₃ | F | p-F-phenyl |
| 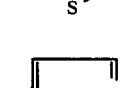 | (CH₂)₂CH₃ | —(CH₂)₃— | | F | 2,2,2-F₃-1-phenylethyl |
| 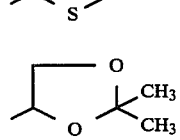 | CH₂CH₃ | CH₃ | CH₃ | H | Isopropyl |
| 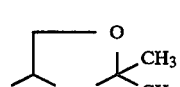 | (CH₂)₂CH₃ | n-C₃H₇ | H | F | Pyridin-3-yl |
| 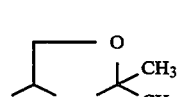 | CH₂CH₃ | H | H | F | Cyclohexyl |
| 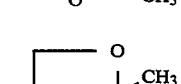 | (CH₂)₂CH₃ | —(CH₂)₃— | | H | 4-Cl-Phenyl |
| 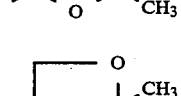 | CH₂CH₃ | H | CH₃ | F | 3-CH₃-pent-3-yl |
| 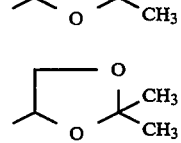 | (CH₂)₂CH₃ | H | H | H | Cyclohex-2-en-1-yl |
|  | CH₂CH₃ | CH₃ | CH₃ | F | Phenyl |
|  | (CH₂)₂CH₃ | C₂H₅ | CH₃ | F | 1-Cl-tert.-Butyl |

TABLE B-continued $$\text{I (W} = -\text{C}\equiv\text{C}-)$$

Structure: cyclohexenone with HO, R¹ substituent, R² on carbon, =N-O-CH(R³)-C(R⁴)=C(R⁵)-C≡C-R⁶

$$\text{I (W} = -\text{CH}=\text{CH}-)$$

Structure: cyclohexenone with HO, R¹ substituent, R² on carbon, =N-O-CH(R³)-C(R⁴)=C(R⁵)-CH=CH-R⁶

| R¹ | R² | R³ | R⁵ | R⁴ | R⁶ |
|---|---|---|---|---|---|
| 1,3-dioxolan-2-ylmethyl (tetrahydro) | CH₂CH₃ | CH₃ | H | F | Cyclopentyl |
| 1,3-dioxolan-2-ylmethyl | (CH₂)₂CH₃ | H | H | F | Phenyl |
| 1,3-dioxolan-2-ylmethyl | CH₂CH₃ | CH₃ | H | F | tert.-Butyl |
| 1,3-dioxolan-2-ylmethyl | (CH₂)₂CH₃ | C₂H₅ | H | H | n-Hexyl |
| 1,3-dioxolan-2-ylmethyl | CH₂CH₃ | H | CH₃ | F | p-F-phenyl |
| 1,3-dioxolan-2-ylmethyl | (CH₂)₂CH₃ | —(CH₂)₃— | | F | 2,2,2-F₃-1-phenylethyl |
| Cyclohexyl | CH₂CH₃ | CH₃ | CH₃ | H | 1-CH₃O-eth-1-yl |
| Cyclohexyl | (CH₂)₂CH₃ | n-C₃H₇ | H | F | Pyridin-3-yl |
| Cyclohexyl | CH₂CH₃ | H | H | F | Cyclohexyl |
| Cyclohexyl | (CH₂)₂CH₃ | —(CH₂)₃— | | H | 4-Cl-phenyl |
| Cyclohexyl | CH₂CH₃ | H | CH₃ | F | 3-CH₃-pent-3-yl |

TABLE B-continued
I (W = —C≡C—)
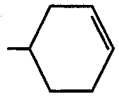
I (W = —CH=CH—)
| R¹ | R² | R³ | R⁵ | R⁴ | R⁶ |
|---|---|---|---|---|---|
| 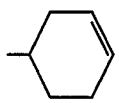 | (CH₂)₂CH₃ | H | H | H | Cyclohex-2-en-1-yl |
| 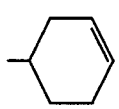 | CH₂CH₃ | CH₃ | CH₃ | F | Phenyl |
| 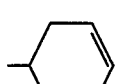 | (CH₂)₂CH₃ | C₂H₅ | CH₃ | F | 1-Cl-tert.-Butyl |
| 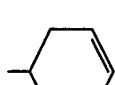 | CH₂CH₃ | CH₃ | H | F | Cyclopentyl |
| 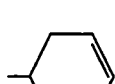 | (CH₂)₂CH₃ | H | CH₃ | CH₃ | p-F-Phenyl |
| 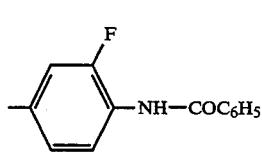 | CH₂CH₃ | CH₃ | CH₃ | F | p-Cl-Phenyl |
| 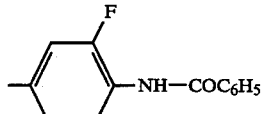 | (CH₂)₂CH₃ | H | H | H | tert.-Butyl |
| 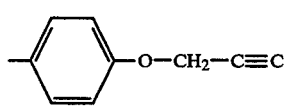 | (CH₂)₂CH₃ | H | H | F | Phenyl |
|  | CH₂CH₃ | CH₃ | H | F | tert.-Butyl |
|  | (CH₂)₂CH₃ | C₂H₅ | H | H | n-Hexyl |

TABLE B-continued

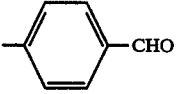

I (W = —C≡C—)

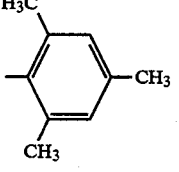

I (W = —CH=CH—)

| R$^1$ | R$^2$ | R$^3$ | R$^5$ | R$^4$ | R$^6$ |
|---|---|---|---|---|---|
| 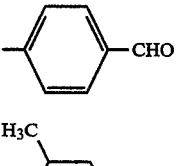 | CH$_2$CH$_3$ | H | CH$_3$ | F | p-F-phenyl |
| 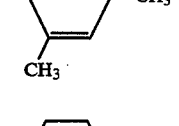 | (CH$_2$)$_2$CH$_3$ | —(CH$_2$)$_3$— | | F | 2,2,2-F$_3$-1-phenylethyl |
| 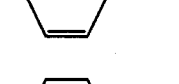 | CH$_2$CH$_3$ | CH$_3$ | CH$_3$ | H | 1-CH$_3$O-eth-1-yl |
| 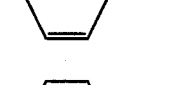 | (CH$_2$)$_2$CH$_3$ | n-C$_3$H$_7$ | H | F | Pyridin-3-yl |
| 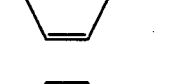 | CH$_2$CH$_3$ | H | H | F | Cyclohexyl |
|  | (CH$_2$)$_2$CH$_3$ | —(CH$_2$)$_3$— | | H | p-Cl-phenyl |
|  | CH$_2$CH$_3$ | H | CH$_3$ | F | 3-CH$_3$-pent-3-yl |
| 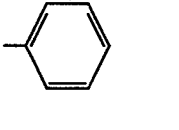 | (CH$_2$)$_2$CH$_3$ | H | H | H | Cyclohex-2-en-1-yl |
| 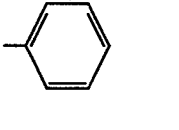 | CH$_2$CH$_3$ | CH$_3$ | CH$_3$ | F | Phenyl |
| 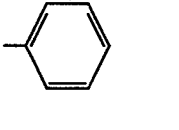 | (CH$_2$)$_2$CH$_3$ | C$_2$H$_5$ | CH$_3$ | F | 1-Cl-tert.-Butyl |

TABLE B-continued

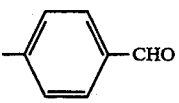

| R¹ | R² | R³ | R⁵ | R⁴ | R⁶ |
|---|---|---|---|---|---|
| (4-CHO-phenyl)- | CH$_2$CH$_3$ | CH$_3$ | H | F | Cyclopentyl |
| (4-(O—CH$_2$—C≡C—H)-phenyl)- | (CH$_2$)$_2$CH$_3$ | H | CH$_3$ | F | 4-F-phenyl |

Unsaturated cyclohexenone oxime ethers I where R³ is hydrogen, R⁴ is hydrogen or fluorine, R⁵ is hydrogen or methyl and R⁶ is hydrogen, methyl or halogen-substituted phenyl are very particularly preferred.

The preparation of compounds I may result in mixtures of the E and Z isomers thereof, where the isomers differ by the cis or trans position of the substituents on the double bond or bonds in the amine ether moiety. The isomers can, if required, be separated by the methods customary for this purpose, eg. by crystallization or chromatography.

The unsaturated cyclohexenone oxime ethers I can be obtained in a variety of ways, preferably by reacting alkylcarbonyl-substituted cyclohexanediones II with hydroxylamines III

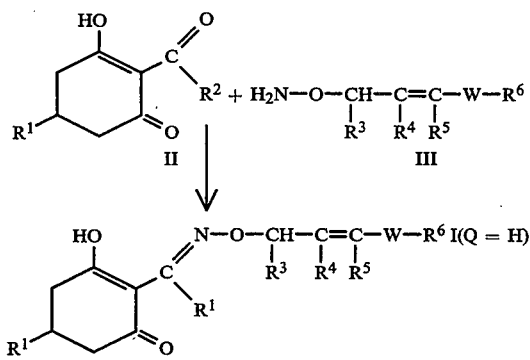

The reaction is carried out in a conventional manner (cf. EP-A 169 521) in an inert solvent or diluent in the presence of a base.

Suitable solvents are dimethyl sulfoxide, alcohols such as methanol, ethanol, isopropanol and cyclohexanol, aliphatic hydrocarbons such as n-hexane and cyclohexane, aromatic hydrocarbons such as toluene and o-, m- and p-xylene, chlorohydrocarbons such as methylene chloride and 1,2-dichloroethane, esters such as methyl acetate, nitriles such as acetonitrile, cyclic ethers such as dioxane and tetrahydrofuran, and mixtures of the said solvents. The reaction mixture comprises one or two phases depending on the solvent used.

Examples of suitable bases are alkali metal and alkaline earth metal carbonates such as sodium carbonate, potassium carbonate and calcium carbonate, alkali metal and alkaline earth metal bicarbonates such as sodium bicarbonate and potassium bicarbonate, alkali metal and alkaline earth metal oxides such as sodium oxide, potassium oxide, calcium oxide and magnesium oxide, alkali metal and alkaline earth metal acetates such as sodium acetate, potassium acetate and calcium acetate, alkali metal and alkaline earth metal hydroxides, especially sodium hydroxide and potassium hydroxide, alkali metal and alkaline earth metal alcoholates, especially sodium methanolate, potassium methanolate, sodium ethanolate and potassium ethanolate, and amines such as triethylamine, pyridine and 4-dimethylaminopyridine, specifically in at least the stoichiometric amount based on the amount of II for complete reaction.

The reaction is preferably carried out in methanol with sodium bicarbonate as base, in which case the amount of base is usually from 0.5 to 2 mol % of that of III.

The hydroxylamine III can be employed in the form of the free base, for example dissolved in water, or preferably of a suitable ammonium salt.

The ratios of amounts are not critical. The precursors II and III are normally employed in the stoichiometric ratio, but an excess of up to about 20 mol % of compound III may be advantageous. If the hydroxylamine III is also used as base, a larger excess of it will be present.

The reaction is generally carried out under atmospheric pressure or the autogenous pressure of the particular solvent, and advantageously at from 0° C. to the boiling point of the solvent, in particular from 20° to 80° C.

The reaction mixture is worked up by conventional methods, for example by removing the solvent, partitioning the residue between methylene chloride and water and isolating the product from the organic phase.

The alkylcarbonyl-substituted cyclohexanediones II are disclosed in EP-A 80 301, EP-A 125 094, EP-A 137 174, EP-A 177 913, EP-A 142 741 and U.S. Pat. No. 4,249,937 or can be obtained by conventional methods, for example by reacting cyclohexane-1,3-diones IV with acid chlorides V and subsequent rearrangement with certain imidazole or pyridine derivatives (cf. JP-A 79/063052):

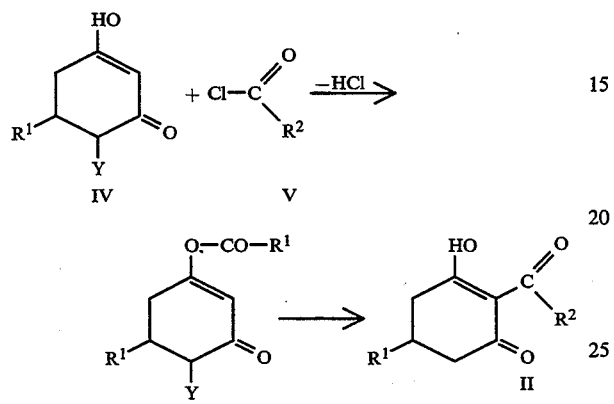

Y = hydrogen or methoxycarbonyl.

Another possible way of preparing the alkylcarbonyl-substituted cyclohexanediones II from the cyclohexane-1,3-diones IV is described in Tetrahedron Lett. (1975) 2491.

The hydroxylamines IIIa

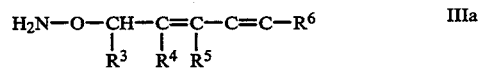

which contain a double and a triple bond, are disclosed in EP-A 341 048 and EP-A 361 827, or can be prepared by the methods described therein.

The hydroxylamines IIIb

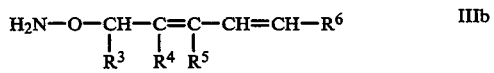

which contain two double bonds, are novel. They can be obtained by conventional methods, for example by reacting vinylmagnesium chloride with cinnamaldehyde VI, treating the product VII with aqueous hydrobromic acid [cf. Chem. Reviews 56 (1956) 753], converting the resulting brominated diene VIII into a phthalimide IX and then liberating the hydroxylamine [cf. EP-A 244 786]:

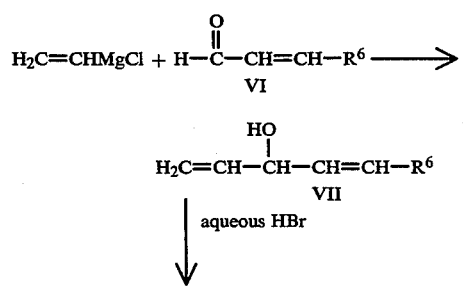

-continued

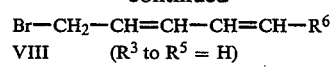

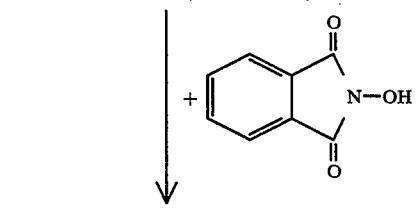

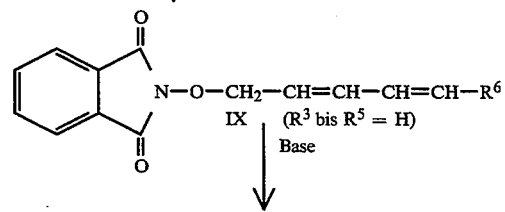

The brominated dienes of the formula VIII and the phthalimides of the formula IX

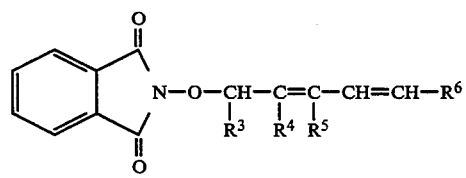

are also novel.

The unsaturated cyclohexenone oxime ethers I can be converted into their alkali metal salts by reaction with, for example, alkali metal hydroxides such as sodium and potassium hydroxide and alkali metal alcoholates such as sodium and potassium methanolate, in aqueous solution or in an aprotic organic solvent such as methanol, ethanol, acetone, toluene and o-, m- and p-xylene. Other salts of the compounds I, eg. alkaline earth metal salts such as magnesium, calcium and barium salts, transition metal salts such as manganese, iron, copper and zinc salts, ammonium salts with from one to four $C_1$-$C_4$-alkyl, phenyl and/or benzyl substituents such as diisopropylammonium, tetramethylammonium, tetrabutylammonium and trimethylbenzylammonium salts, phosphonium salts and sulfonium salts, especially trialkylsulfonium salts, can be obtained from the alkali metal salts, especially the sodium salts, of the compounds I.

Unsaturated cyclohexenone oxime ethers I where Q is $C_1$-$C_6$-alkylcarbonyl or benzoyl can be prepared by conventional esterification of compounds I where Q is hydrogen using $C_1$-$C_6$-alkanecarboxylic acids or benzoic acid.

The unsaturated cyclohexenone derivatives I are suitable as herbicides, especially for controlling graminaceous plants (grasses). They are generally tolerated and thus selective in broad-leaved crops and in monocotyledonous crops which do not belong to the family of Graminaceae. However, some derivatives of the compounds I may display selectivity in Graminaceae, which makes specific control of unwanted grasses possible.

The unsaturated cyclohexenone oxime ethers I and the herbicidal agents containing them can be applied, for example, in the form of directly sprayable solutions, powders, suspensions, including high-percentage aqueous, oily or other suspensions or dispersions, emulsions, oil dispersions, pastes, dusting or broadcasting agents or granules by spraying, atomizing, dusting, broadcasting or watering. The application forms depend on the purpose for which they are used; they ought in every case to ensure the finest possible distribution of the active ingredients according to the invention.

The compounds I are generally suitable for preparing directly sprayable solutions, emulsions, pastes or oil dispersions. Suitable inert additives are mineral oil fractions of moderate to high boiling point such as kerosene or diesel oil, also coaltar oils and oils of vegetable or animal origin, aliphatic, cycloaliphatic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or highly polar solvents such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. To prepare emulsions, pastes or oil dispersions, the substances can be homogenized, as such or dissolved in an oil or solvent, using wetting agents, adhesion promoters, dispersants or emulsifiers, in water. However, it is also possible to prepare concentrates which are composed of active substance, wetting agent, adhesion promoter, dispersant or emulsifier and, where appropriate, solvent or oil and which are suitable for dilution with water.

Suitable surfactants are the alkali metal, alkaline earth metal and ammonium salts of aromatic sulfonic acids, eg. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, products of the condensation of sulfonated naphthalene and its derivatives with formaldehyde, products of the condensation of naphthalene or naphthalenesulfonic acids with phenol and formaldehyde, polyoxyethylene octylphenol ether, ethoxylated isooctyl-, octal- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders and dusting and broadcasting agents can be prepared by mixing or grinding the active substances together with a solid carrier.

Granules, eg. coated, impregnated or homogeneous granules, can be prepared by binding the active ingredients to solid carriers. Examples of solid carriers are mineral earths such as silica gel, silicic acids, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The formulations generally contain from 0.01 to 95% by weight, preferably from 0.5 to 90% by weight, of active ingredient. The active ingredients are employed in a purity of from 90 to 100%, preferably 95 to 100% (according to the NMR spectrum).

Examples of formulations are:

I. a solution of 90 parts by weight of compound No. 1.01 and 10 parts by weight of N-methyl-α-pyrrolidone is suitable for use in the form of very small drops;

II. a mixture of 20 parts by weight of compound No. 1.02, 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil. A fine dispersion of the mixture in 100,000 parts by weight of water contains 0.02% by weight of active ingredient;

III. an aqueous dispersion of 20 parts by weight of compound No. 1.03, 40 parts by weight of cyclohexanone, 30 parts by weight of isobutanol, 20 parts by weight of the adduct of 40 moles of ethylene oxide and 1 mole of castor oil. A mixture of this dispersion with 100,000 parts by weight of water contains 0.02% by weight of the active ingredient;

IV. an aqueous dispersion of 20 parts by weight of compound No. 1.04, 25 parts by weight of cyclohexanol, 65 parts by weight of a mineral oil fraction of boiling point 210° to 280° C. and 10 parts by weight of the adduct of 40 moles of ethylene oxide and 1 mole of castor oil. A mixture of this dispersion with 100,000 parts by weight of water contains 0.02% of the active ingredient;

a mixture, ground in a hammer mill, of 80 parts by weight of compound No. 1.05, 3 parts by weight of sodium diisobutylnaphthalene-α-sulfonate, 10 parts by weight of the sodium salt of a ligninsulfonic acid from a sulfite waste liquor and 7 parts by weight of powdered silica gel. A fine dispersion of this mixture in 20,000 parts by weight of water contains 0.1% by weight of the active ingredient and can be used for spraying;

VI. an intimate mixture of 3 parts by weight of compound No. 1.06 and 97 parts by weight of finely divided kaolin. This dusting agent contains 3% by weight of active ingredient;

VII. an intimate mixture of 30 parts by weight of compound No. 1.07, 92 parts by weight of powdered silica gel and 8 parts by weight of liquid paraffin which was sprayed onto the surface of this silica gel. This formulation confers good adhesion on the active ingredient;

VIII. a stable aqueous dispersion of 40 parts by weight of compound No. 1.08, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of compound No. 1.09, 2 parts by weight of calcium dodecylbenzenesulfonic acid, 8 parts by weight of fatty alcohol polyglycol ether, 20 parts by weight of the sodium salt of a phenolsulfonic acid/urea/formaldehyde condensate and 68 parts by weight of a liquid paraffin;

a mixture, ground in a hammer mill, of 10 parts by weight of compound No. 1.10, 4 parts by weight of sodium diisobutylnaphthalene-α-sulfonate, 20 parts by weight of the sodium salt of a ligninsulfonic acid from a sulfite waste liquor, 38 parts by weight of silica gel and 38 parts by weight of kaolin. A fine dispersion of the mixture in 10,000 parts by weight of water contains 0.1% by weight of active ingredient and can be used for spraying.

The herbicidal agents or the active ingredients can be applied by a pre-emergence or post-emergence process. If the active ingredients are less well tolerated by certain crop plants, it is possible to use application techniques in which the herbicidal agents are sprayed in such a way that the leaves of the sensitive crop plants are touched as little as possible while the active ingredients reach the leaves of unwanted plants underneath or the bare soil (post-directed, lay-by).

The application rates for the active ingredient depend on the aim of the control, the season, the target plants and the stage of growth and are from 0.001 to 3.0, preferably 0.01 to 1, kg/ha of active substance.

In view of the wide variety of application methods, the unsaturated cyclohexenone oxime ethers or the agents containing them can also be employed in a number of other crop plants for removing unwanted plants. Examples of suitable crops are the following:

| Botanical name | English name |
|---|---|
| *Allium cepa* | cooking onion |
| *Ananas comosus* | pineapple |
| *Arachis hypogaea* | peanut |
| *Asparagus officinalis* | asparagus |
| *Beta vulgaris* spp. *altissima* | sugar beet |
| *Beta vulgaris* spp. *rapa* | fodder beet |
| *Brassica napus* var. *napus* | rape |
| *Brassica napus* var. *napobrassica* | Swedish turnip |
| *Brassica rapa* var. *silvestris* | turnip rape |
| *Camellia sinensis* | tea plant |
| *Carthamus tinctorius* | safflower |
| *Carya illinoinensis* | pecan nut |
| *Citrus limon* | lemon |
| *Citrus sinensis* | orange |
| *Coffea arabica* (*Coffea canephora, Coffea liberica*) | coffee |
| *Cucumis sativus* | cucumber |
| *Cynodon dactylon* | Bermuda grass |
| *Daucus carota* | carrot |
| *Elaeis guineensis* | oil palm |
| *Fragaria vesca* | strawberry |
| *Glycine max* | soybean |
| *Gossypium hirsutum* (*Gossypium arboreum, Gossypium herbaceum, Gossypium vitifolium*) | cotton |
| *Helianthus annuus* | sunflower |
| *Hevea brasiliensis* | para rubber tree |
| *Hordeum vulgare* | barley |
| *Humulus lupulus* | hops |
| *Juglans regia* | walnut |
| *Lens culinaris* | lentil |
| *Linum usitatissimum* | flax |
| *Lycopersicon lycopersicum* | tomato |
| *Malus* spp. | apple |
| *Manihot esculenta* | cassava |
| *Medicago sativa* | alfalfa |
| *Musa* spp. | bananas |
| *Nicotiana tabacum* (*N. rustics*) | tobacco |
| *Olea europaea* | olive |
| *Oryza sativa* | rice |
| *Phaseolus lunatus* | lima bean |
| *Phaseolus vulgaris* | bush bean |
| *Picea abies* | spruce |
| *Pinus* spp. | pines |
| *Pisum sativum* | garden pea |
| *Prunus avium* | sweet cherry |
| *Prunus persica* | peach |
| *Pyrus communis* | pear |
| *Ribes sylvestre* | redcurrant |
| *Ricinus communis* | castor oil |
| *Saccharum officinarum* | sugar cane |
| *Secale cereale* | rye |

-continued

| Botanical name | English name |
|---|---|
| *Solanum tuberosum* | potato |
| *Sorghum bicolor* (*S. vulgars*) | sorghum |
| *Theobroma cacao* | cocoa |
| *Trifolium pratense* | red clover |
| *Triticum aestivum* | wheat |
| *Triticum durum* | durum wheat |
| *Vicia faba* | horse bean |
| *Vitis vinifera* | grapevine |
| *Zea mays* | corn |

To extend the spectrum of action and to achieve synergistic effects, the unsaturated cyclohexenone oxime ethers I can be mixed and applied together with many representatives of other groups of herbicides or growth regulators. Examples of suitable mixing partners are diazines, 4H-3,1-benzoxazine derivatives, benzothiadiazinones, 2,6-dinitroanilines, N-phenylcarbamates, thiocarbamates, halo carboxylic acids, triazines, amides, ureas, diphenyl ethers, triazinones, uracils, benzofuran derivatives, cyclohexane-1,3-dione derivatives, quinolinecarboxylic acid derivatives, imidazolinones, sulfonamides, sulfonylureas, aryloxy- and hetaryloxyphenoxypropionic acids and the salts, esters and amides thereof, and others.

It may also be beneficial to apply the compounds I, alone or in combination with other herbicides, mixed together with other crop protection agents, for example with agents for controlling pests or phytopathogenic fungi or bacteria. Also of interest is the miscibility with mineral salt solutions which can be employed to eliminate deficiencies in nutrients and trace elements. It is also possible to add non-phytotoxic oils and oil concentrates.

PREPARATION EXAMPLES

EXAMPLE 1

2-[(Z)-3-Methylpent-3-en-1-yn-5-yloxyiminobutyl]-3-hydroxy-5-(2-H-tetrahydropyran-4-yl)-2-cyclohexen-1-one

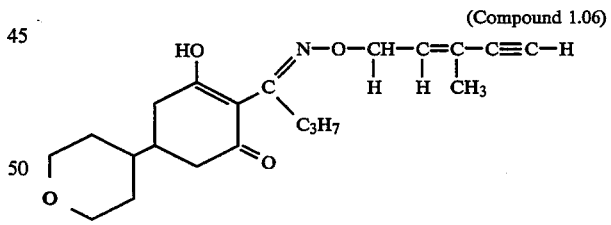

(Compound 1.06)

A mixture of 3 g (11 mmol) of 2-butyryl-3-hydroxy-5-(2H-tetrahydropyran-4-yl)-2-cyclohexen-1-one and 1.5 g (13 mmol) of (Z)-5-aminooxy-3-methylpent-3-en-1-yne in 100 ml of methanol was stirred at 25° C. for 16 hours. The solvent was removed and then the residue was taken up in 100 ml of 10% by weight aqueous sodium hydroxide solution. The aqueous phase was extracted three times with 100 ml of methylene chloride each time and then acidified (pH=1) with concentrated hydrochloric acid while cooling with ice and then extracted three times with 100 ml of diethyl ether each time. The combined organic phases were worked up in a conventional manner to give the product. The crude product was purified by chromatography on silica gel (ethyl acetate as eluent).

Yield: 73%; 300 MHz $^1$H NMR (in CDCl$_3$, TMS as standard): 1.95 ppm (s,3H); 3.20 (s,1H); 4.75 (d,2H); 5.90 (t,1H).

Precursor 1α: N-(Z)-(3-Methylpent-3-en-1-yn-5-yloxy)phthalimide

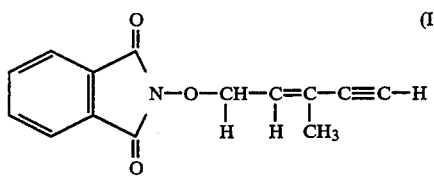

(Intermediate 3.01)

71.8 g (0.44 mol) of N-hydroxyphthalimide and 115.4 g (0.44 mol) of triphenylphosphine were added to a solution of 40.0 g (0.4 mol) of 5-hydroxy-3-methylpent-3-en-1-yne in 960 ml of anhydrous tetrahydrofuran. 85.2 g (0.44 mol) of diethyl azodicarboxylate were added dropwise to this mixture over the course of 3 hours in such a way that the temperature did not exceed 35° C. The reaction mixture was subsequently stirred overnight and then the solvent was removed under reduced pressure, and 400 ml of toluene were added to the residue. After removal of insolubles, the organic phase was washed twice with 5% by weight aqueous sodium hydroxide solution and once with saturated aqueous sodium chloride solution and then worked up in a conventional manner to give the product. Purification was by chromatography on silica gel N 60 (eluent:toluene) followed by recrystallization from isopropanol.

Yield: 48%; melting point: 102°–103° C. 250 MHz $^1$H NMR (in d$^6$-DMSO): 1.85 ppm (s,3H); 4.24 ppm (s,1H); 4.82 ppm (d,2H); 6.08 ppm (t,1H); 7.88 ppm (s,4H).

Precursor 1β: (Z)-5-Aminooxy-3-methylpent-3-en-1-yne

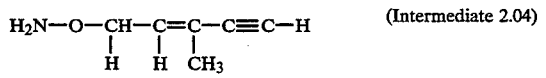

(Intermediate 2.04)

A mixture of 45 g (0.19 mol) of N-(Z)-(3-methylpent-3-en-1-yn-5-yloxy)phthalimide and 95 ml (1.57 mol) of ethanolamine was stirred at about 20° C. for 4 hours and then poured into 300 ml of ice-cold saturated sodium chloride solution. The product was extracted from the aqueous phase with 3×100 ml of dichloromethane. The combined organic phases were washed with saturated aqueous sodium chloride solution and dried over magnesium sulfate. Removal of the solvent under reduced pressure yielded the product as an oil.

Yield: 63% 250 MHz $^1$H NMR (in CDCl$_3$, TMS as standard): 1.93 ppm (s,3H); 3.2 ppm (s,1H); 4.38 ppm (d,2H); 5.4 ppm (broad, 2H); 5.9 ppm (t,1H).

EXAMPLE 2

E,E-N-[5-(4-fluorophenyl)-2,4-pentadienyloxy]phthalimide

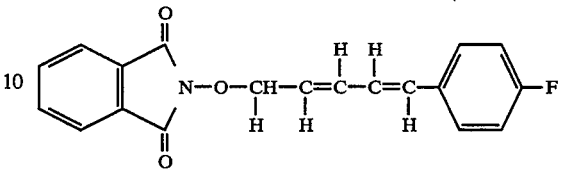

(Intermediate 3.02)

8.3 ml (60 mmol) of triethylamine were added dropwise at about 20° C. to a mixture of 10.4 g (43 mmol) of 1-bromo-5-(4-fluorophenyl)-2,4-pentadiene, 9.8 g (60 mmol) of N-hydroxyphthalimide and 45 ml of N-methylpyrrolidone. The mixture was stirred for 24 hours and then poured into 200 ml of water and extracted several times with ethyl acetate, after which the combined organic phases were washed with 5% by weight aqueous sodium hydroxide solution and then with saturated aqueous sodium chloride solution. After drying with magnesium sulfate and removal of the solvent, the residue was recrystallized from 70 ml of ethanol. Yield: 57%. Melting point: 155°–157° C.

Precursor 2α: 1-Bromo-5-(4-fluorophenyl)-2,4-pentadiene

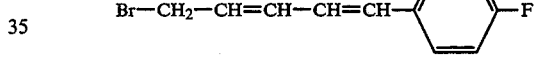

40 ml of 47% by weight aqueous hydrobromic acid and 80 ml of toluene were successively added to 20 g (0.11 mol) of 1-(4-fluorophenyl)-1,4-pentadien-3-ol. After 10 minutes, the phases were separated and then the organic phase was washed with saturated aqueous sodium bicarbonate solution, dried with sodium sulfate and concentrated under reduced pressure.

Yield: 18.6 g (crude product).

Precursor 2β: 1-(4-Fluorophenyl)-1,4-pentadien-3-ol

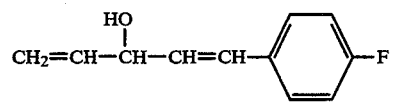

350 ml of a 1.6 molar solution of vinylmagnesium chloride (=0.55 mol of vinylmagnesium chloride) were added dropwise at 0° to 5° C. to a solution of 75 g (0.5 mol) of 4-fluorocinnamaldehyde in 100 ml of tetrahydrofuran. After stirring for 4 hours at 25° C., hydrolysis was carried out at 0° to 5° C. with 150 ml of saturated aqueous ammonium chloride solution, and then the phases were separated and the organic phase was dried with sodium sulfate. After removal of the solvent under reduced pressure, the residue was distilled under 0.2 torr; boiling point 92° C., yields 41 g.

Table 1 which follows lists further compounds I which were or can be prepared in the same way. Tables 2 and 3 contain further intermediates III and IX.

TABLE 1

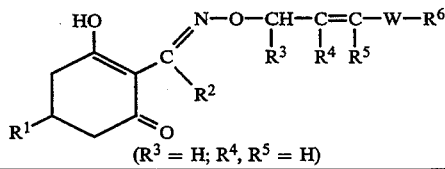

(R³ = H; R⁴, R⁵ = H)

| No. | R¹ | R² | W | R⁶ | Config. | Physic. data (300 MHz ¹H NMR [ppm]*) |
|---|---|---|---|---|---|---|
| 1.01 | tetrahydrothiopyranyl (S) | Ethyl | —C≡C— | CH₃ | Z | 1.95(s, 3H), 3.20(s, 1H), 4.75(d, 2H), 5.90(t, 1H) |
| 1.02 | tetrahydrothiopyranyl (S) | Propyl | —C≡C— | CH₃ | Z | 1.95(s, 3H), 3.20(s, 1H), 4.75(d, 2H), 5.90(t, 1H) |
| 1.03 | tetrahydropyranyl (O) | Ethyl | —C≡C— | CH₃ | Z | 1.95(s, 3H), 3.20(s, 1H), 4.75(d, 2H), 5.90(t, 1H) |
| 1.04 | tetrahydropyranyl (O) | Propyl | —C≡C— | CH₃ | Z | 1.95(s, 3H), 3.20(s, 1H), 4.75(d, 2H), 5.90(t, 1H) |
| 1.05 | tetrahydropyranyl (O) | Ethyl | —C≡C— | CH₃ | Z | 1.95(s, 3H), 3.20(s, 1H), 4.75(d, 2H), 5.90(t, 1H) |
| 1.06 | tetrahydropyranyl (O) | Propyl | —C≡C— | CH₃ | Z | 1.95(s, 3H), 3.20(s, 1H), 4.75(d, 2H), 5.90(t, 1H) |
| 1.07 | tetrahydrothiopyranyl (S) | Ethyl | E—CH=CH— | 4-F-phenyl | E | 1.15(t, 3H), 4.62(d, 2H), 5.95(dt, 1H) |
| 1.08 | tetrahydrothiopyranyl (S) | Propyl | E—CH=CH— | 4-F-phenyl | E | 0.95(t, 3H), 4.6(d, 2H), 5.95(dt, 1H) |
| 1.09 | tetrahydropyranyl (O) | Ethyl | E—CH=CH— | 4-F-phenyl | E | 1.15(t, 3H), 4.62(d, 2H), 5.95(dt, 1H) |
| 1.10 | tetrahydropyranyl (O) | Propyl | E—CH=CH— | 4-F-phenyl | E | 0.95(t, 3H), 4.62(d, 2H), 5.95(dt, 1H) |
| 1.11 | tetrahydrothiopyranyl (S) | Ethyl | —C≡C— | CH₃ | E | |
| 1.12 | tetrahydrothiopyranyl (S) | Propyl | —C≡C— | CH₃ | E | |

TABLE 1-continued

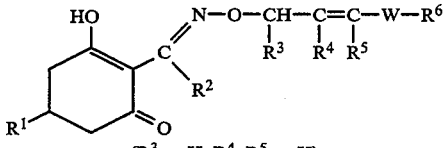

($R^3$ = H; $R^4$, $R^5$ = H)

| Nr. | $R^1$ | $R^2$ | W | $R^5$ | Config. |
|---|---|---|---|---|---|
| 1.13 | tetrahydropyran-4-yl | Ethyl | —C≡C— | $CH_3$ | E |
| 1.14 | tetrahydropyran-4-yl | Propyl | —C≡C— | $CH_3$ | E |
| 1.15 | $CH_3CH_2$-S-CH($CH_2$—)- | Propyl | —C≡C— | $CH_3$ | E |
| 1.16 | 2,4,6-$(CH_3)_3$-Cyclohexyl | Ethyl | —C≡C— | $CH_3$ | E |

| Nr. | $R^1$ | $R^2$ | W | $R^3$ | $R^4$ | $R^5$ | $R^6$ | Config. | Physic. data (300 MHz-$^1$H-NMR [ppm]*)) |
|---|---|---|---|---|---|---|---|---|---|
| 1.20 | tetrahydropyran-4-yl | Propyl | —C≡C— | H | H | $CH_3$ | 4-Cl-phenyl | Z | 0.95(t), 2.0(s), 4.8(d), 5.9(t) |
| 1.21 | $CH_3CH_2$-S-CH($CH_2$—)- | Propyl | —C≡C— | H | H | $CH_3$ | 4-Cl-phenyl | Z | 0.95(t), 2.0(s), 4.8(d), 5.9(t) |
| 1.22 | 2,4,6-$(CH_3)_3$-phenyl | Ethyl | —C≡C— | H | H | $CH_3$ | 4-Cl-phenyl | Z | 1.2(t), 2.0(s), 4.8(d), 5.95(t) |
| 1.23 | 2,4,6-$(CH_3)_3$-phenyl | Ethyl | —C≡C— | H | H | $CH_3$ | 4-Cl-phenyl | Z | 1.15(t), 1.9(s), 4.65(d), 6.1(t) |
| 1.24 | tetrahydrothiopyran-4-yl | Ethyl | —C≡C— | H | H | $CH_3$ | 4-F-phenyl | E | 1.1(t), 2.0(s), 4.8(d), 5.9(t) |
| 1.25 | tetrahydrothiopyran-4-yl | Propyl | —C≡C— | H | H | $CH_3$ | 4-F-phenyl | E | 0.95(t), 2.0(s), 4.8(d), 5.9(t) |
| 1.26 | tetrahydropyran-4-yl | Propyl | —C≡C— | H | H | $CH_3$ | 4-F-phenyl | E | 0.95(t), 2.0(s), 4.8(d), 5.9(t) |
| 1.27 | tetrahydropyran-4-yl | Ethyl | —C≡C— | H | H | $CH_3$ | 4-F-phenyl | Z | 1.15(t), 2.0(s), 3.35(t), 4.8(d), 7.0(m) |
| 1.28 | $CH_3CH_2$-S-CH($CH_2$—)- | Propyl | —C≡C— | H | H | $CH_3$ | 4-F-phenyl | Z | 0.95(t), 2.0(s), 4.8(d), 7.05(m) |
| 1.29 | tetrahydrothiopyran-4-yl | Propyl | —C≡C— | H | H | $CH_3$ | 1-OH-2,2,6,6-$(CH_3)_4$-Cyclohexyl | Z | 0.95(t), 1.1(s), 1.15(s), 4.75(d), 5.8(m) |

TABLE 1-continued $$\text{(I)}$$

Structure: cyclohexenone with HO, R¹ substituent, C(R²)=N-O-CH(R³)-C(R⁴)=C(R⁵)-W-R⁶

(R³ = H; R⁴, R⁵ = H)

| No. | R¹ | R² | | R³ | R⁴ | R⁵ | R⁶ | W | NMR |
|---|---|---|---|---|---|---|---|---|---|
| 1.30 | 3-tetrahydrothiopyranyl | Ethyl | —C≡C— | H | H | CH₃ | 1-OH-2,2,6,6-(CH₃)₄-Cyclohexyl | Z | 1.1(s), 1.15(s), 4.75(d), 5.8(m) |
| 1.31 | 4-tetrahydropyranyl | Ethyl | —C≡C— | H | H | CH₃ | 1-OH-2,2,6,6-(CH₃)₄-Cyclohexyl | Z | 1.1(s), 1.15(s), 3.35(t), 4.7(d) |
| 1.32 | 4-tetrahydropyranyl | Propyl | —C≡C— | H | H | CH₃ | 1-OH-2,2,6,6-(CH₃)₄-Cyclohexyl | Z | 0.95(s), 1.1(s), 1.15(s), 3.35(t), 4.7(d) |
| 1.33 | 4-tetrahydropyranyl | Ethyl | —C≡C— | H | H | CH₃ | 1-OH-cyclohexyl | Z | 1.15(t), 1.9(s), 3.35(t), 4.7(d), 5.8(m) |
| 1.34 | 4-tetrahydropyranyl | Propyl | —C≡C— | H | H | CH₃ | 1-OH-cyclohexyl | Z | 0.95(t), 1.9(s), 3.35(t), 4.7(d), 5.8(m) |
| 1.35 | 3-tetrahydrothiopyranyl | Propyl | —C≡C— | H | H | CH₃ | 1-OH-cyclohexyl | Z | 0.95(t), 1.9(s), 4.7(d), 5.8(m) |
| 1.36 | 3-tetrahydrothiopyranyl | Ethyl | E—C≡C— | H | H | H | Ethyl | E | 1.0(t), 1.15(t), 4.55(d), 5.85(m) |
| 1.37 | 3-tetrahydrothiopyranyl | Propyl | E—C≡C— | H | H | H | Ethyl | E | 0.95(t), 1.0(t), 4.55(d), 5.85(m) |
| 1.38 | 4-tetrahydropyranyl | Ethyl | E—C≡C— | H | H | H | Ethyl | E | 1.0(t), 1.15(t), 3.35(t), 4.55(d), 5.85(m) |
| 1.39 | 4-tetrahydropyranyl | Propyl | E—C≡C— | H | H | H | Ethyl | E | 0.95(t), 1.0(t), 3.35(t), 4.55(d), 5.85(m) |
| 1.40 | 3-tetrahydrothiopyranyl | Ethyl | E—C≡C— | H | H | H | Methyl | E | |
| 1.41 | 3-tetrahydrothiopyranyl | Propyl | E—C≡C— | H | H | H | Methyl | E | |

TABLE 1-continued $$\underset{R^1}{\overset{HO}{\diagdown}}\overset{N-O-CH-C=C-W-R^6}{\underset{R^2}{\overset{|}{C}}\overset{|}{\underset{R^3}{\overset{|}{R^4}}\overset{|}{R^5}}} \tag{I}$$

($R^3$ = H; $R^4$, $R^5$ = H)

| No. | $R^1$ | $R^2$ | | $R^4$ | $R^5$ | $R^6$ | W | NMR*) |
|---|---|---|---|---|---|---|---|---|
| 1.42 | 4-tetrahydropyranyl (O) | Ethyl | E—C≡C— | H | H | H | Methyl | E | |
| 1.43 | 4-tetrahydropyranyl (O) | Propyl | E—C≡C— | H | H | H | Methyl | E | |
| 1.44 | 3-tetrahydrothiopyranyl (S) | Ethyl | —C≡C— | H | H | CH₃ | 4-F-phenyl | E | 1.15(t), 1.99(s), 4.68(d), 6.08(t) |
| 1.45 | 3-tetrahydrothiopyranyl (S) | Propyl | —C≡C— | H | H | CH₃ | 4-F-phenyl | E | 0.97(t), 1.98(s), 4.67(d), 6.08(t) |
| 1.46 | 4-tetrahydropyranyl (O) | Ethyl | —C≡C— | H | H | CH₃ | 4-F-phenyl | E | 1.14(t), 1.97(s), 3.37(t), 3.99(dd), 4.67(d), 6.09(t) |
| 1.47 | 4-tetrahydropyranyl (O) | Propyl | —C≡C— | H | H | CH₃ | 4-F-phenyl | E | |
| 1.48 | 1-CH₃S-cyclopropyl | Ethyl | —C≡C— | H | H | CH₃ | H | E | 0.74(m), 1.13(t), 1.88(s), 2.09(s), 2.9(s), 4.63(d) |
| 1.49 | 1-CH₃S-cyclopropyl | Propyl | —C≡C— | H | H | CH₃ | H | E | 0.74(m), 0.98(t), 1.9(s), 2.12(s), 2.9(s), 4.63(d) |
| 1.50 | 3-tetrahydrothiopyranyl (S) | Ethyl | —C≡C— | H | H | CH₃ | 1-OH-cyclohexyl | Z | 1.15(t), 1.9(s), 4.7(d), 5.8(m) |
| 1.51 | 3-tetrahydrothiopyranyl (S) | Ethyl | —C≡C— | H | H | CH₃ | 4-Cl-phenyl | E | |
| 1.52 | 3-tetrahydrothiopyranyl (S) | Propyl | —C≡C— | H | H | CH₃ | 4-Cl-phenyl | E | |
| 1.53 | 4-tetrahydropyranyl (O) | Ethyl | —C≡C— | H | H | CH₃ | 4-Cl-phenyl | E | |
| 1.54 | 4-tetrahydropyranyl (O) | Propyl | —C≡C— | H | H | CH₃ | 4-Cl-phenyl | E | |

*) in CDCl₃, TMS as internal standard

TABLE 2

$$H_2N-O-CH_2-CH=\underset{\underset{R^5}{|}}{C}-W-R^6 \quad (III) \quad (R^3, R^4 = H; W = -C\equiv C- \text{ oder } -CH=CH-)$$

| Nr. | $R^5$ | $R^6$ | W | Config. | Yield | Physic. data (300 MHz-$^1$H-NMR [δ in ppm]/m.p.) |
|---|---|---|---|---|---|---|
| 2.01 | $CH_3$ | H | $-C\equiv C-$ | E | 90% | oil; 1.8(s, 3H), 2.88(s, 1H), 4.26(d, 2H), 5.45(s, 2H), 6.08(t, 1H) |
| 2.02 | $CH_3$ | 4-F-phenyl | $-C\equiv C-$ | E | | oil; 1.87(s, 3H), 4.21(d, 2H), 6.1(m, 3H), 7.15–7.6(2m, 4H) |
| 2.03 | $CH_3$ | 4-Cl-phenyl | $-C\equiv C-$ | E | | |
| 2.04 | $CH_3$ | H | $-C\equiv C-$ | Z | 63% | 1.9(s); 3.2(s); 4.35(d) |
| 2.05 | $CH_3$ | 4-F-phenyl | $-C\equiv C-$ | Z | | oil; 1.99(s, 3H), 4.23(d, 2H), 5.45(s, 2H), 5.91(t, 1H), 6.9–7.5(2m, 4H) |
| 2.06 | $CH_3$ | 4-Cl-phenyl | $-C\equiv C-$ | Z | 92% | oil; 2.0(s, 3H), 4.45(d, 2H), 5.4(s, 2H), 5.91(t, 1H), 7.2–7.5(m, 4H) |
| 2.07 | H | 4-F-phenyl | $E-CH=CH-$ | E | 91% | 54–56° C., NMR: 4.26(d, 2H), 5.4(s, 2H), 5.8–6.0(m, 1H), 6.3–6.8(m, 3H), 6.9–7.5(m, 4H) |
| 2.08 | H | $CH_3$ | $E-CH=CH-$ | E | | |
| 2.09 | H | $C_2H_5$ | $E-CH=CH-$ | E | | |
| 2.10 | $CH_3$ | 1-OH-cyclo-hexyl | $-C\equiv C-$ | Z | | 1.9(s), 4.35(d), 5.45(bs), 5.8(m) |
| 2.11 | $CH_3$ | 1-OH-2,2,6,6-$(CH_3)_4$-cyclohexyl | $-C\equiv C-$ | Z | | |

TABLE 3

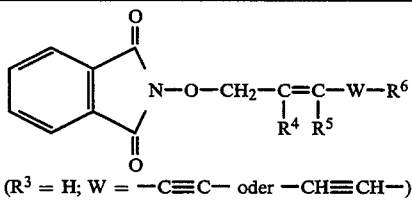

(IX)

$(R^3 = H; W = -C\equiv C- \text{ oder } -CH\equiv CH-)$

| Nr. | $R^4$ | $R^5$ | $R^6$ | W | Config. | Yield | Physic. data (250 MHz-$^1$H-NMR [in ppm]/m.p.) |
|---|---|---|---|---|---|---|---|
| 3.01 | H | $CH_3$ | H | $-C\equiv C-$ | Z | 48% | 102–103° C.; NMR: 1.85(s, 3H), 4.24(s, 1H), 4.82(d, 2H), 6.08(t, 1H), 7.88(s, 4H) |
| 3.02 | H | H | 4-F-phenyl | $E-CH=CH-$ | E | 57% | 155–157° C.; NMR: 4.77(d, 2H), 5.9–6.1(m, 1H), 6.4–6.7(m, 2H), 6.8–7.0(m, 1H), 7.1–7.6(2m, 4H), 7.85(s, 4H) |
| 3.03 | H | $CH_3$ | 4-Cl-phenyl | $-C\equiv C-$ | Z | 50% | 109–111° C.; NMR: 1.83(s, 3H), 4.92(d, 2H), 6.1(t, 1H), 7.3–7.55(m, 4H), 7.8(s, 4H) |
| 3.04 | H | $CH_3$ | H | $-C\equiv C-$ | E | 66% | 122–124° C.; NMR: 1.84(s, 3H), 4.04(s, 1H), 4.77(d, 2H), 6.08(t, 1H), 7.8(s, 4H) |
| 3.05 | H | $CH_3$ | 1-OH-cyclohexyl | $-C\equiv C-$ | Z | | NMR: 1.9(s), 4.9(d), 5.95(m), 7.85(m), |
| 3.06 | H | H | $CH_3$ | $E-CH=CH-$ | E | | |
| 3.07 | H | H | $C_2H_5$ | $E-CH=CH-$ | E | | |
| 3.08 | H | $CH_3$ | 1-OH-2,2,6,6-$(CH_3)_4$-Cyclohexyl | $-C\equiv C-$ | Z | | |
| 3.09 | H | $CH_3$ | 4-F-phenyl | $-C\equiv C-$ | Z | | 102–104° C.; NMR: 1.93(s, 3H), 4.4(d, 2H), 6.09(t, 1H), 7.2–7.5(2m, 4H), 7.81(s, 4H) |
| 3.10 | H | $CH_3$ | 4-Cl-phenyl | $-C\equiv C-$ | E | | |
| 3.11 | H | $CH_3$ | 4-F-phenyl | $-C\equiv C-$ | E | | NMR: 1.96(s, 3H), 4.86(d, 2H), 6.16(t, 1H), 7.2–7.7(2m, 4H), 7.81(s, 4H) |

EXAMPLE 3 cis-5-(4-Chlorophenyl)-3-methylpent-2-en-4-yn-1-ol

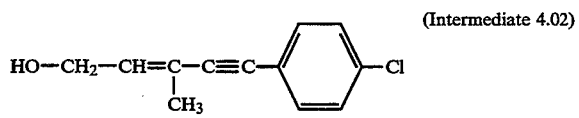

(Intermediate 4.02)

46.1 g (0.48 mol) of cis-3-methyl-2-penten-4-yn-1-ol were added dropwise over the course of 25 minutes to a mixture of 76.6 g (0.4 mol) of 1-chloro-4-bromobenzene, 1.2 g (1.7 mmol) of $Pd[P(C_6H_5)_3]_2Cl_2$, 2.6 g (13 mmol) of copper(I) iodide, 6 g (20 mmol) of triphenylphosphine and 200 ml of triethylamine at 50° to 60° C. The reaction mixture was heated at 90° C. for 5 hours and then methyl tert-butyl ether/water was added, after which the phases were separated. The organic phase was washed with saturated aqueous ammonium chloride solution and then with saturated aqueous sodium bicarbonate solution and was worked up in a conventional manner to give the product. Yield: 99.7 g (containing 70% product).

The crude product can be used without further purification for the synthesis of the cyclohexanediones I.

Other important intermediates are listed in Table 4.

TABLE 4

| No. | $R^6$ | W | ($R^3$, $R^4$ = H; $R^5$ = $CH_3$; W = $-C\equiv C-$, $-C=C-$) Config. | Physic. data |
|---|---|---|---|---|
| 4.01 | 4-F-phenyl | $-C\equiv C-$ | Z | |
| 4.02 | 4-Cl-phenyl | $-C\equiv C-$ | Z | |

EXAMPLES OF USE (herbicidal activity)

The herbicidal action of the unsaturated cyclohexenone oxime ethers of the formula I was demonstrated in glasshouse tests:

The seeds of the test plants were sown in plastic flowerpots containing loamy sand with about 3% humus as substrate, keeping the species separate.

In the case of pre-emergence treatment, the active ingredients suspended or emulsified in water were applied immediately after sowing using fine nozzles. The pots were lightly watered to promote germination and growth and then covered with transparent plastic covers until the plants had started to grow. This covering results in uniform germination of the test plants unless this is impaired by the active ingredients.

For post-emergence treatment, the test plants were grown in the test pots or transplanted into them a few days beforehand. The active ingredients, suspended or emulsified in water, were applied when the plants were from 3 to 15 cm high, depending on the species. The application rate for post-emergence treatment was 0.5 kg/ha active ingredient.

The plants were kept at 10°-25° C. or 20°-35° C., depending on the species. The test lasted from 2 to 4 weeks, during which the plants were tended and their reaction to the individual treatments was evaluated.

A scale from 0 to 100 was used for the evaluation, 100 meaning no emergence of the plants or complete destruction at least of the above-ground parts and 0 meaning no damage or normal growth.

The plants used in the glasshouse tests belong to the following species:

| Botanical name | English name |
|---|---|
| *Avena sativa* | oats (volunteer crop) |
| *Echinochloa crus-galli* | Japanese millet |

The results showed that compounds Nos. 1.01, 1.02 and 1.03 are very useful for controlling graminaceous plants by the post-emergence method.

We claim:

1. An unsaturated cyclohexenone oxime ether of the formula I

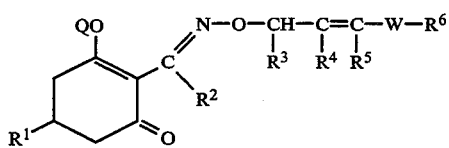

where

Q is hydrogen, $C_1-C_6$-alkylcarbonyl, benzoyl, an alkali metal or alkaline earth metal ion, an ammonium ion whose nitrogen may be unsubstituted or substituted by one to four $C_1-C_4$-alkyl, phenyl or benzyl substituents or mixtures thereof, or a phosphonium, sulfonium or sulfoxonium ion or an equivalent of a transition metal cation;

W is $-C\equiv C-$ or $-CH=CH-$;

$R^1$ is $C_3-C_7$-cycloalkyl, a 6-membered heterocyclic group which has one oxygen atom as the only ring hetero atom and can be saturated, partially unsaturated or aromatic, the cyclic groups being optionally substituted by one to three of the following: hydroxyl, halogen, $C_1-C_4$-alkyl, partially or completely halogenated $C_1-C_4$-alkyl, $C_1-C_4$-alkoxy or $C_1-C_4$-alkylthio; a 5-membered saturated heterocycle which has one oxygen hetero atom and is optionally substituted by one to three of the following: $C_1-C_4$-alkyl, partially or completely halogenated $C_1-C_4$-alkyl, $C_1-C_4$-alkoxy or $C_1-C_4$-alkylthio; a 5-membered heteroaromatic group which has one oxygen atom as the only ring hetero atom and is optionally substituted by one to three of the following: cyano, halogen, $C_1-C_4$-alkyl, partially or completely halogenated $C_1-C_4$-alkyl, $C_2-C_6$-alkenyl, partially or completely halogenated $C_2-C_6$-alkenyl, $C_1-C_4$-alkoxy, $C_1-C_4$-alkylthio, $C_2-C_6$-alkenyloxy or $C_1-C_4$-alkoxy-$C_1-C_4$-alkyl; phenyl unsubstituted or substituted by one to three of the following: nitro, cyano, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_1-C_4$-alkoxy-$C_1-C_4$-alkyl, $C_1-C_4$-alkylthio-$C_1-C_4$-alkyl, $C_3-C_6$-alkenyloxy, $C_3-C_6$-alkynyloxy or $-NR^8R^9$ where $R^8$ is hydrogen and $R^9$ is benzoyl;

$R^2$ is $C_1-C_6$-alkyl;

$R^3$ is hydrogen or $C_1-C_6$-alkyl $R^4$ is hydrogen, halogen or $C_1-C_4$-alkyl;

$R^5$ is hydrogen or $C_1-C_6$-alkyl;

or $R^3$ and $R^4$, $R^3$ and $R^5$ or $R^4$ and $R^5$ together form $C_2-C_4$-alkylene or $C_2-C_4$-alkenylene;

$R^6$ is hydrogen, $C_1-C_6$-alkyl, partially or completely halogenated $C_1-C_4$-alkyl which may be optionally substituted by a phenyl radical, or $C_2-C_6$-alkenyl, $C_1-C_4$-alkoxy-$C_1-C_4$-alkyl, $C_1-C_4$-alkylthio-$C_1-C_4$-alkyl, $C_3-C_7$-cycloalkyl or $C_5-C_7$-cycloalkenyl, wherein either the cycloalkyl or cycloalkenyl may be optionally substituted by one to three of the following: hydroxyl, $C_1-C_4$-alkyl, partially or completely halogenated $C_1-C_4$-alkyl, $C_1-C_4$-alkoxy, $C_1-C_4$-alkoxy-$C_1-C_4$-alkyl or $C_1-C_4$-alkylthio-$C_1-C_4$-alkyl; phenyl or pyridyl, wherein either the phenyl or the pyridyl may be optionally substituted by one to three of the following: nitro, cyano, hydroxyl, halogen, $C_1-C_4$-alkyl, partially or completely halogenated $C_1-C_4$-alkyl, $C_1-C_4$-alkoxy, $C_1-C_4$-alkylthio, $C_1-C_4$-alkoxy-$C_1-C_4$-alkyl or $C_1-C_4$-alkylthio-$C_1-C_4$-alkyl.

2. A herbicidal composition containing a liquid or solid carrier and an effective amount of at least one unsaturated cyclohexenone oxime ether of the formula I as defined in claim 1.

3. A process for controlling unwanted plant growth, which compromises applying a herbicidally effective amount of an unsaturated cyclohexenone oxime ether of the formula I as defined in claim 1 to unwanted plants, their habitat or on their seeds.

* * * * *

UNITED STATES PATENT AND TRADEMARK OFFICE
CERTIFICATE OF CORRECTION

PATENT NO.: 5,407,896

DATED: April 18, 1995

INVENTOR(S): KAST et al.

It is certified that error appears in the above-identified patent and that said Letters Patent is hereby corrected as shown below:

Column 56, claim 1, line 12, between "oxygen" and "hetero" insert --atom as the only ring--.

Column 56, claim 1, line 19, "$C_1$-$_{C4}$-alkyl" should be --$C_1$-$C_4$-alkyl--.

Signed and Sealed this

Twentieth Day of June, 1995

*Attest:*

BRUCE LEHMAN

*Attesting Officer*    *Commissioner of Patents and Trademarks*